United States Patent
Liu et al.

(10) Patent No.: US 9,913,811 B2
(45) Date of Patent: Mar. 13, 2018

(54) HYDROXYNAPHTHOQUINONE COMPOUNDS FOR TREATMENT OF NON-SMALL CELL LUNG CANCER

(71) Applicant: Macau University of Science and Technology, Taipa (MO)

(72) Inventors: Liang Liu, Taipa (MO); Lai Han Leung, Taipa (MO); Xia Li, Taipa (MO); Xing-Xing Fan, Taipa (MO)

(73) Assignee: Macau University of Science and Technology, Taipa (MO)

( * ) Notice: Subject to any disclaimer, the term of this patent is extended or adjusted under 35 U.S.C. 154(b) by 0 days.

(21) Appl. No.: 15/186,795

(22) Filed: Jun. 20, 2016

(65) Prior Publication Data

US 2017/0360721 A1 Dec. 21, 2017

(51) Int. Cl.
*A61K 31/122* (2006.01)

(52) U.S. Cl.
CPC .................. *A61K 31/122* (2013.01)

(58) Field of Classification Search
USPC ........................................ 514/7.6, 19.3, 738
See application file for complete search history.

(56) References Cited

FOREIGN PATENT DOCUMENTS

WO WO 2013/152186 A1 * 10/2013 ............... C12Q 1/32

OTHER PUBLICATIONS

Guo; Zhong Xi Yi Jie He Za Zhi; Oct. 1991; 11(10):598-9, 580) (abstract).*
Lan; Cell Biochemistry and Biophysics; 2014, 70, 1459-1467.*
Tian; Bioscience Reports; 2015, 35, e00189, doi 10.1042/BSR20150002; published on Feb. 27, 2015.*

\* cited by examiner

*Primary Examiner* — Pancham Bakshi
(74) *Attorney, Agent, or Firm* — Renner Kenner Greive Bobak Taylor & Weber

(57) ABSTRACT

A compound suitable for treating EGFR-dependent non-small cell lung cancer exceptionally inhibits activity of the EGFR kinase, in particular in EGFR-dependent non-small cell lung cancer with intrinsic or acquired resistance against at least one EGFR inhibitor. Methods for inhibiting EGFR kinase activity in non-small cell lung cancer cells which harbor an abnormality in the EGFR gene and for targeting cancer cells harboring an abnormality in EGFR gene by contacting EGFR-dependent non-small cell lung cancer cells with said compound are also provided. The compounds allow for an advantageous inhibition of the EGFR kinase activity and induction of apoptosis of the non-small cell lung cancer cells with abnormality in the EGFR gene. Hence, said compounds represent a highly promising treatment option for patients harboring EGFR-dependent cancer.

20 Claims, 15 Drawing Sheets

HYDROXYNAPHTHOQUINONE COMPOUNDS FOR TREATMENT OF NON-SMALL CELL LUNG CANCER

TECHNICAL FIELD

The present invention relates to the administration of a hydroxynaphthoquinone compound and its effect on subjects with EGFR-dependent non-small cell lung cancer. More specifically, the present invention is directed to a method comprising administering a hydroxynaphthoquinone compound for treating a subject suffering from EGFR-dependent non-small cell lung cancer. The present invention further provides a method of inhibiting EGFR kinase activity in non-small cell lung cancer cells harboring an abnormality in EGFR gene and a method for targeting cancer cells from non-small-cell lung cancer harboring an abnormality in EGFR gene.

BACKGROUND OF INVENTION

Lung cancer is the leading cause of cancer-related mortality in China and the world, wherein non-small cell lung cancer (NSCLC), in particular NSCLC adenocarcinoma, accounts for the majority of all cases. More specifically, NSCLC is the dominate type of lung cancer with about 85% among all lung cancers.

Over the past decade, it has become evident that subtypes of NSCLC can be further defined at the molecular level by recurrent "driver mutations" that occur in oncogenes like tyrosine kinases. There are more than 90 kinds of receptor tyrosine kinases which are related to NSCLC. EGFR mutations represent the most common type of driver mutations for NSCLC. It is assumed that about 10% Caucasian patients and 30-40% East Asian patients with NSCLC harbor EGFR mutations increasing the activity of EGFR leading to hyper-activation of the signaling pathways downstream to EGFR (e.g. Cross, D. A. et al., Cancer Discovery, 2014, 4(9):1046-1061).

EGFR belongs to a family of receptor tyrosine kinases, namely the ErbB family, a subfamily of four closely related receptor tyrosine kinases: EGFR (ErbB-1), HER2/c-neu (ErbB-2), Her3 (ErbB-3) and Her4 (ErbB-4) (Zhang H, et al., J. Clin. Invest. 117 (August 2007) (8): 2051-2058). EGFR is located on the surface of the cells and is activated by binding of specific ligands and dimerization, which stimulates its intrinsic intracellular protein-tyrosine kinase activity and anti-apoptotic and growth-stimulating pathways downstream to EGFR involving, for example, the phosphoinositide 3-kinase (PI3K)-AKT pathway, the STAT pathway and the MAPK pathway. This includes transautophosphorylation of some tyrosine (Y) residues in the C-terminal domain of EGFR, which include Y992, Y1045, Y1068, Y1148 and Y1173 (Herbst R S (2004). Int. J. Radiat. Oncol. Biol. Phys. 59 (2 Suppl): 21-6. doi:10.1016/j.ijrobp.2003.11.041. PMID 15142631, Tam I. Y. et al., Molecular Cancer Therapeutics, 2009, 8(8):2142-51).

Modern technology has highly improved the efficacy of treatments in NSCLC, but new challenge comes up, such as chemo-resistance and cancer relapse (Mulshine, J. L., Lung Cancer, 2003, 41 suppl 1(2):S163-74, Dragnev, K. et al., Expert Opinion on Investigational Drugs, 2013, 22(1):35-47).

The majority of EGFR mutations are non-overlapping with other mutations found in NSCLC like KRAS mutations, ALK rearrangement and the like. Some of the EGFR mutations do not reduce or increase the efficacy of EGFR inhibitors (tyrosine kinase inhibitors (TKI) of EGFR) like gefitinib, erlotinib or afatinib (Oda, K. et al., Mol. Syst. Biol. 1 (1): 2005.0010. doi:10.1038/msb4100014. PMC 1681468. PMID 16729045, Cross, D. A. et al., Cancer Discovery, 2014, 4(9):1046-1061). Other mutations reduce the efficacy of EGFR inhibitors or prevent them from working, i.e. are associated with a resistance against the EGFR inhibitor(s). An example is the T790M substitution, a point mutation in exon 20 of EGFR, as one of the mechanisms of resistance against EGFR inhibitors. There are some similar mutations associated with a resistance against EGFR inhibitors, which are D761Y, L747S and T854A etc (Li, D et al., Oncogene, 2008, 27(34):4702-4711).

A large number of clinical trials and the NCCN guidelines recommend EGFR inhibitors in patients with EGFR mutations associated with efficacy or increased efficacy of EGFR inhibitors. Although preclinical studies have shown encouraging results, resistant clinical research is not satisfactory (Jackman, D. M. et al., Clin. Cancer Res. (August 2009) 15 (16): 5267-73. doi:10.1158/1078-0432.CCR-09-0888, PMC 3219530. PMID 19671843). This is because a lot of such patients have or have developed a resistance against EGFR inhibitors in particular due to an acquired T790M mutation and/or MET gene amplification or other mechanisms. Thus, mutations usually associated with an efficacy and/or increased efficacy of EGFR inhibitors often show acquired resistance against EGFR inhibitors and patients who initially responded to EGFR inhibitors might eventually experience disease progression despite continued treatment.

Accordingly, the efficacy of EGFR inhibitors in EGFR-dependent NSCLC is limited in an increasing number of patients. Thus, further potent treatment options for treating EGFR-dependent NSCLC are urgently required. As usual, it would generally be desirable to provide treatment options including compounds with reduced risk for side effects and interactions, which compounds can be prepared in a cost-effective way. Usually, plants and respective ingredients in plants are suitable to provide such advantageous properties and, thus, research also focuses on such materials.

For example, Zi Cao, the dried root of *Arnebia euchroma, Arnebia guttata*, or *Lithospermum erythrorhizon* is already used as a Traditional Chinese medicine with the major component shikonin. The latter possesses antioxidant effects (Assimopoulou, A. N. et al., Food Chemistry (2004) 87 (3): 433-438. doi:10.1016/j.foodchem.2003.12.017), antimicrobial effects against *Staphylococcus aureus* and *Staphylococcus epidermidis*, wound healing, antitumor, and antithrombotic properties (Papageorgiou, V. P. et al., Angew. Chem. Int. Ed. (1999) 38 (3): 270-300. doi:10.1002/(SICI)1521-3773(19990201)38:3<270:AID-ANIE270>3.0.CO; 2-0). Shikonin has been shown to have anti-cancer activity such as in prostate cancer, liver cancer or breast cancer and other cancer cells, but have not been proposed for NSCLC and the specific patent group with EGFR-dependent NSCLC, respectively.

SUMMARY OF INVENTION

The first aspect of the present invention relates to a method of treating EGFR-dependent NSCLC by a compound of Formula (I) in a subject in need thereof, in particular the NSCLC is an adenocarcinoma.

Namely the method of treating a subject suffering from EGFR-dependent NSCLC comprises administering an effective amount of a hydroxynaphthoquinone compound having the structure of Formula (I) or a pharmaceutically acceptable salt, solvate, or anhydrate thereof:

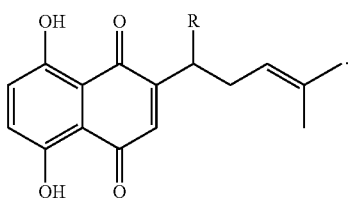

Formula (I)

R is selected from —H, —OH,

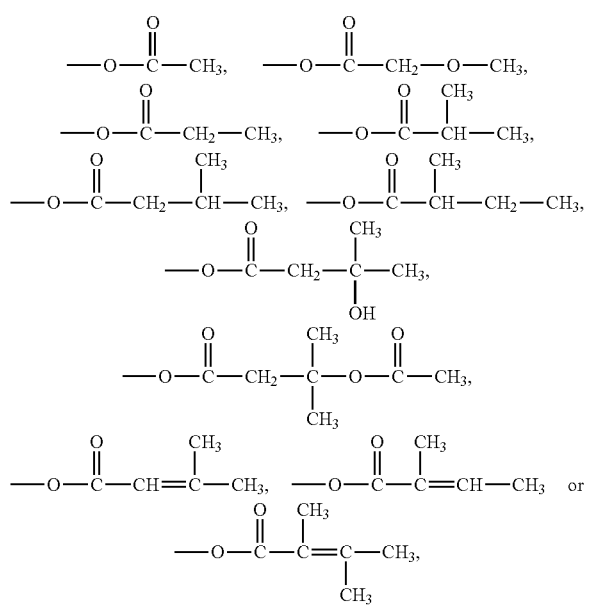

to the subject.

In particular, the compound has the structure of Formula (II):

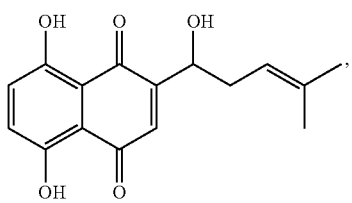

Formula (II)

and comprises a mixture of compounds of Formula (IIa) and Formula (IIb) or is a racemate of compounds of Formula (IIa) and Formula (IIb):

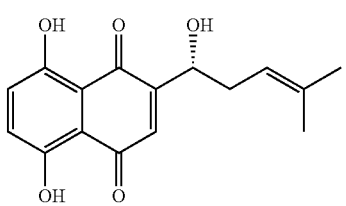

Formula (IIa)

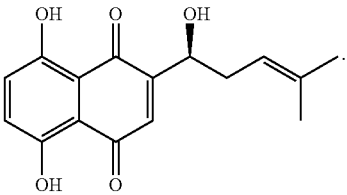

Formula (IIb)

In particular, the compound administered is one of the compound of Formula (IIa) or Formula (IIb).

In still another aspect, the present invention refers to a method of inhibiting EGFR kinase activity in NSCLC cells harboring an abnormality in the EGFR gene by a hydroxynaphthoquinone compound of Formula (I) in a subject in need thereof, i.e. comprising administering an effective amount of the compound of Formula (I) or a pharmaceutically acceptable salt, solvate, or anhydrate thereof:

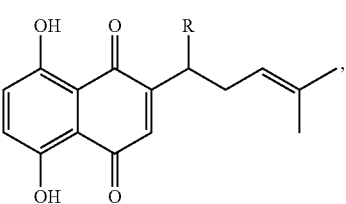

Formula (I)

with R as defined above, in particular a compound of Formula (II) given above, to the subject suffering from EGFR-dependent NSCLC. In one embodiment, the disease is an adenocarcinoma.

According to the invention is also the compound of Formula (I), such as Formula (II), for use in the treatment of EGFR-dependent NSCLC. Furthermore, the invention refers to the use of the compound of Formula (I), such as Formula (II), for preparing a medicament for treatment of EGFR-dependent NSCLC.

The compound of Formula (I), such as of Formula (II), or a salt, solvate or anhydrate thereof can be administered to the subject in form of a pharmaceutical composition. Said pharmaceutical composition further comprises pharmaceutically acceptable excipients and may additionally contain further active ingredients, in particular therapeutic compounds for treating NSCLC. The present invention also refers to the use of the pharmaceutical composition for inhibiting EGFR kinase activity, such as for suppressing transautophosphorylation of EGFR kinase, and/or inhibiting the anti-apoptotic and cell growth stimulating signaling pathway downstream to EGFR.

The present invention, in another aspect, refers to a method for targeting NSCLC cells harboring an abnormality in the EGFR gene, in particular an abnormality in the EGFR gene resulting from at least one mutation selected from deletions in exon 19, substitutions or insertions in exon 20, or substitutions in exon 21 of the EGFR gene, more preferably selected from T790M and/or E746-A750del. Such mutations can further be associated with, in particular, at least one of MET gene amplification and/or FGF2 and FGFR1 induction.

Said method of the present invention comprises the step of contacting said cells with a hydroxynaphthoquinone compound of Formula (I) or a salt, solvate or anhydrate thereof:

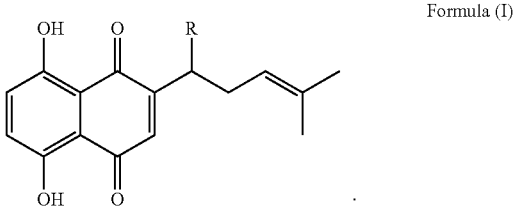

Formula (I)

with R as defined above. In particular, the compound is a compound of Formula (II) given above. Preferably, apoptosis of the NSCLC cells harboring an abnormality in the EGFR gene is induced.

The inventors found that the hydroxynaphthoquinone compound according to the present invention is especially suitable for treating patients with EGFR-dependent NSCLC and for targeting NSCLC cells harboring an abnormality in the EGFR gene, respectively, i.e. cancer and cancer cells with a EGFR mutation, in particular with intrinsic or acquired resistance against EGFR inhibitors such as gefitinib, erlotinib and/or afatinib. More specifically, the inventors found an advantageous inhibitory effect of the hydroxynaphthoquinone compound on EGFR kinase activity and an exceptional induction of apoptosis of the NSCLC cells by the hydroxynaphthoquinone compound. Transautophosphorylation of EGFR could be advantageously reduced with increased EGFR degradation.

Other features and aspects of the invention will become apparent by consideration of the following detailed description and accompanying drawings.

BRIEF DESCRIPTION OF DRAWINGS

FIG. 2A shows a Flow Cytometry pattern of H1650 cells of the control group. FIG. 2B shows a Flow Cytometry pattern of H1650 cells having been treated with 1 µM of the compound of Formula (IIa). FIG. 2C shows a Flow Cytometry pattern of H1650 cells having been treated with 2 µM of the compound of Formula (IIa). FIG. 2D shows a Flow Cytometry pattern of H1650 cells having been treated with 3 µM of the compound of Formula (IIa). FIG. 2E shows a Flow Cytometry pattern of H1650 cells having been treated with 4 µM of the compound of Formula (IIa).

FIG. 3A shows a Flow Cytometry pattern of H1975 cells of the control group. FIG. 3B shows a Flow Cytometry pattern of H1975 cells having been treated with 1 µM of the compound of Formula (IIa). FIG. 3C shows a Flow Cytometry pattern of H1975 cells having been treated with 2 µM of the compound of Formula (IIa). FIG. 3D shows a Flow Cytometry pattern of H1975 cells having been treated with 3 µM of the compound of Formula (IIa). FIG. 3E shows a Flow Cytometry pattern of H1975 cells having been treated with 4 µM of the compound of Formula (IIa).

FIG. 4A shows a Flow Cytometry pattern of H1650 cells of the control group. FIG. 4B shows a Flow Cytometry pattern of H1650 cells having been treated with NAC. FIG. 4C shows a Flow Cytometry pattern of H1650 cells having been treated with 4 µM of the compound of Formula (IIa) in the presence of NAC. FIG. 4D shows a Flow Cytometry pattern of H1650 cells having been treated with 4 µM of the compound of Formula (IIa) in the absence of NAC.

FIG. 5A shows a Flow Cytometry pattern of H1975 cells of the control group. FIG. 5B shows a Flow Cytometry pattern of H1975 cells having been treated with NAC. FIG. 5C shows a Flow Cytometry pattern of H1975 cells having been treated with 4 µM of the compound of Formula (IIa) in the presence of NAC. FIG. 5D shows a Flow Cytometry pattern of H1975 cells having been treated with 4 µM of the compound of Formula (IIa) in the absence of NAC.

DETAILED DESCRIPTION OF INVENTION

Figure 1A:
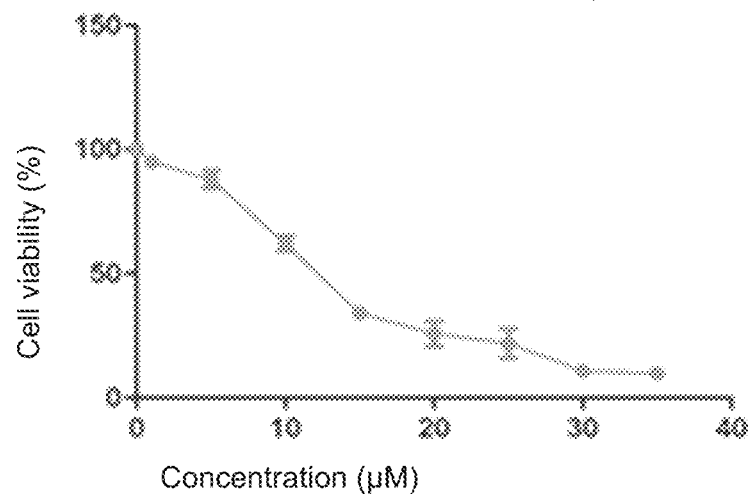
FIG. 1A shows the cell viability of CCD19 cells after 24 hours treatment with the compound of Formula (IIa).
Figure 1B:
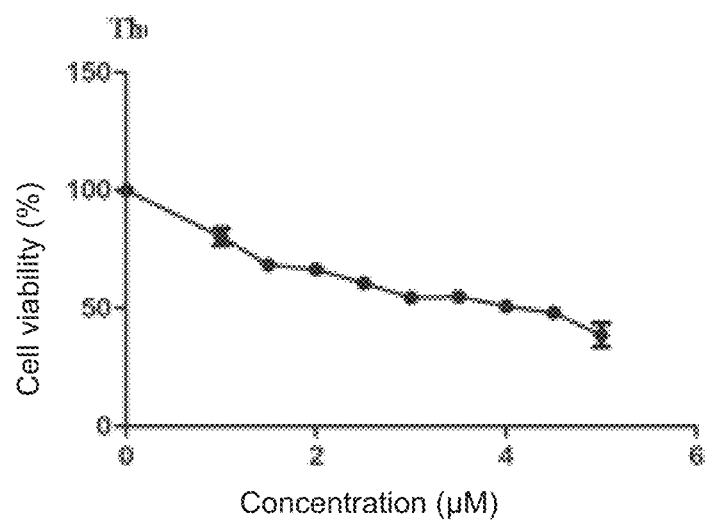
FIG. 1B shows the cell viability of H1650 cells after 24 hours treatment with the compound of Formula (IIa).
Figure 1C:
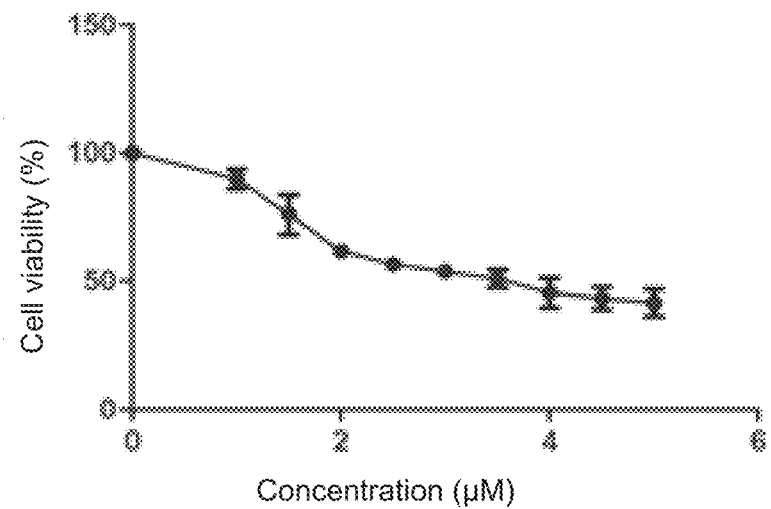
FIG. 1C shows the cell viability of HCC827 cells after 24 hours treatment with the compound of Formula (IIa).
Figure 1D:
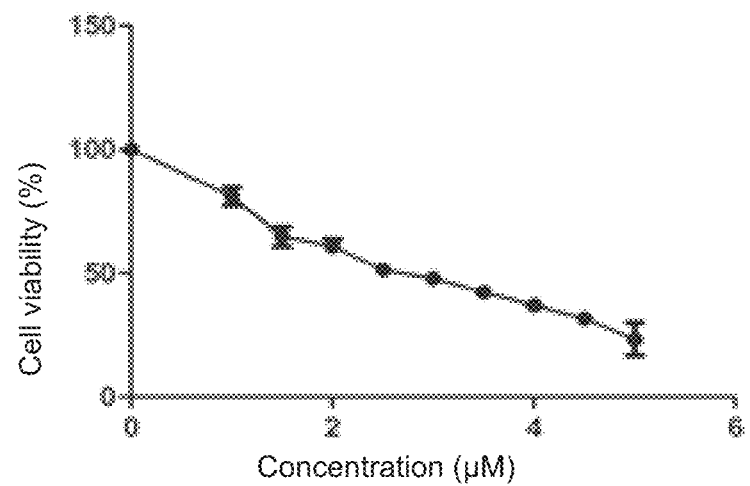
FIG. 1D shows the cell viability of H1975 cells after 24 hours treatment with the compound of Formula (IIa).
Figure 2A:
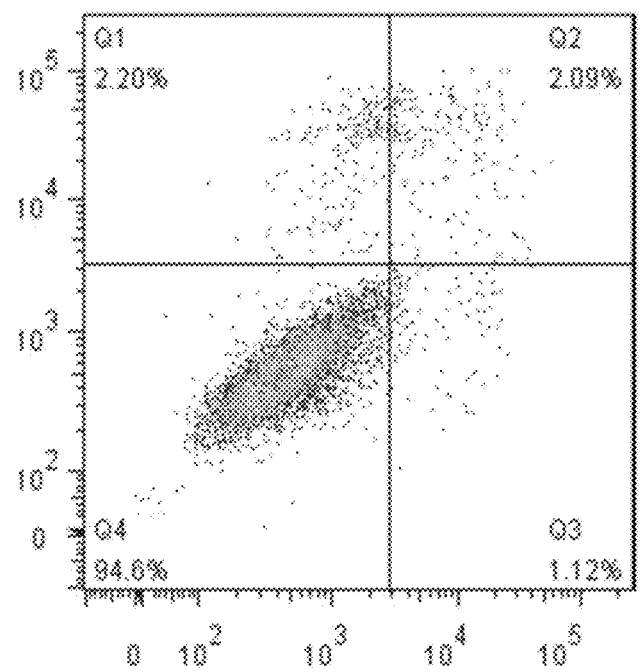
FIGS. 2A, 2B, 2C, 2D, and 2E show Flow Cytometry patterns of H1650 cells having been treated with different concentrations of the compound of Formula (IIa) and of the control group.
Figure 2B:
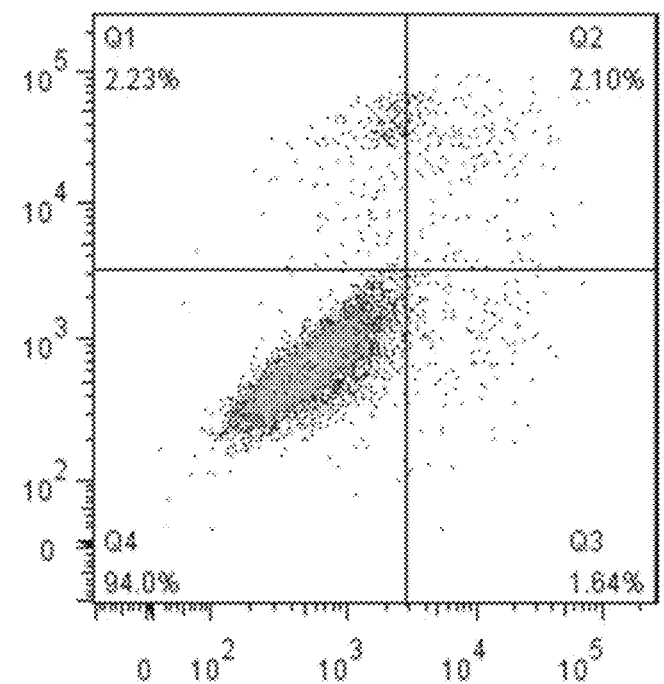
Figure 2C:
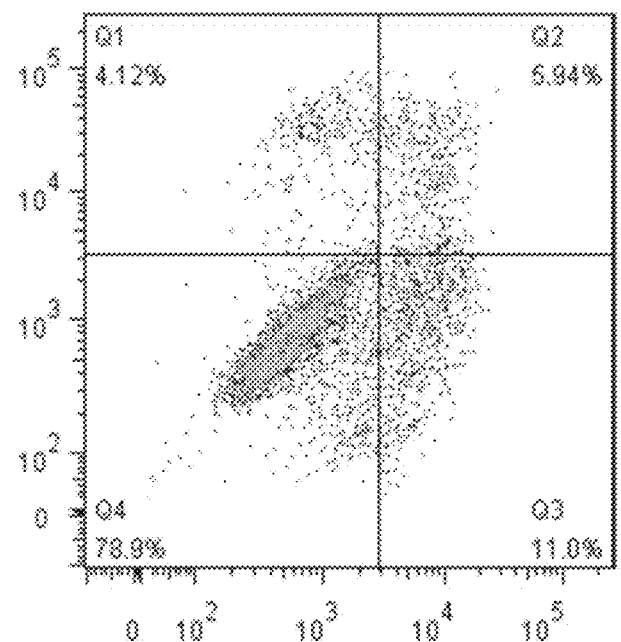
Figure 2D:
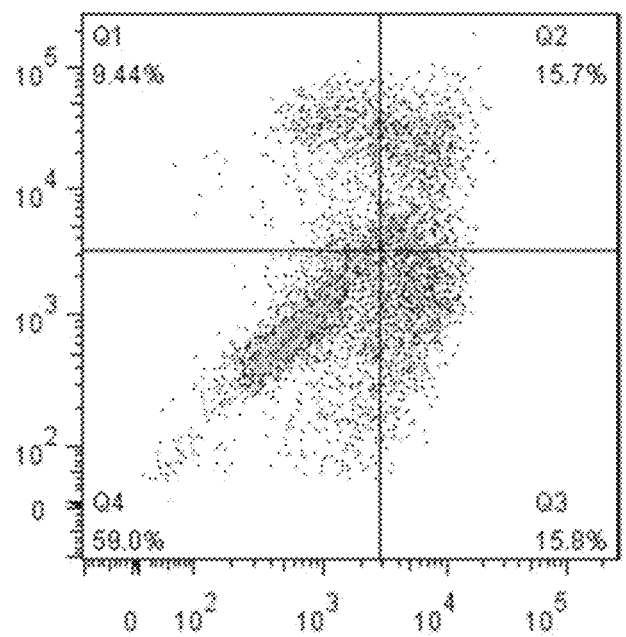
Figure 2E:
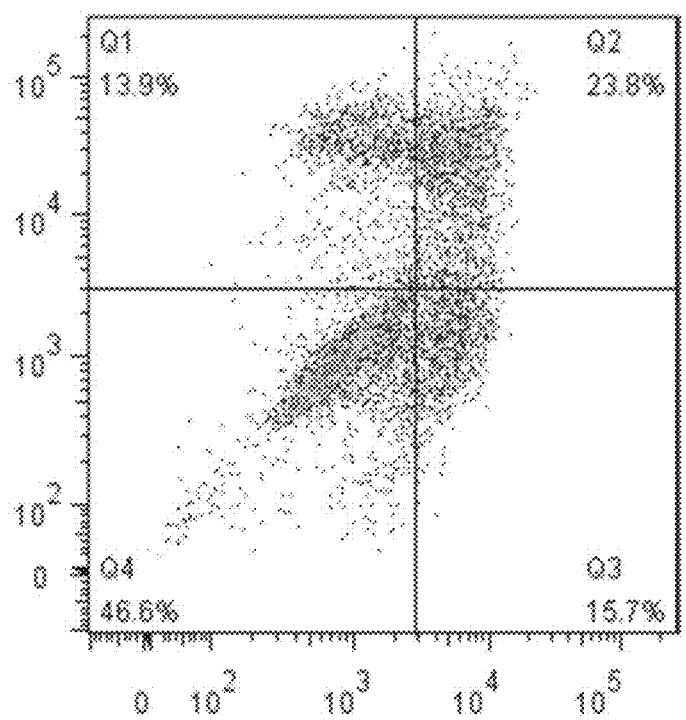
Figure 2F:
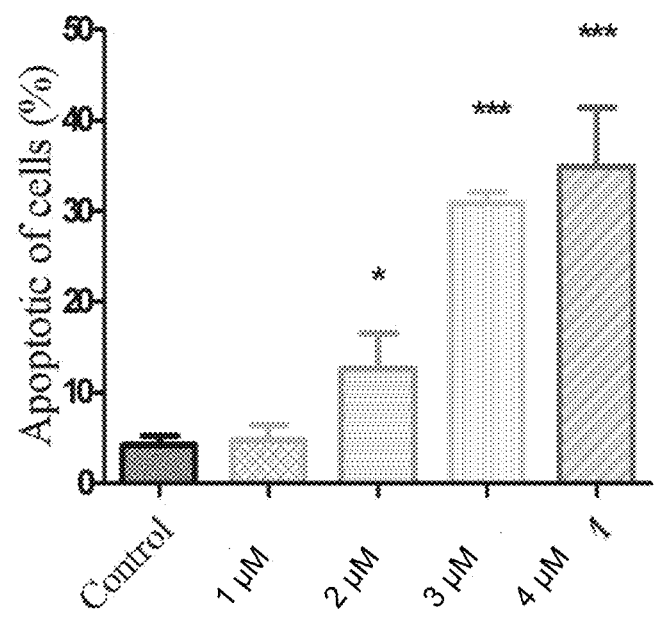
FIG. 2F shows the rate of apoptosis of H1650 cells having been treated with 1 µM, 2 µM, 3 µM or 4 µM of the compound of Formula (IIa) of the present invention compared to the control group.
Figure 3A:
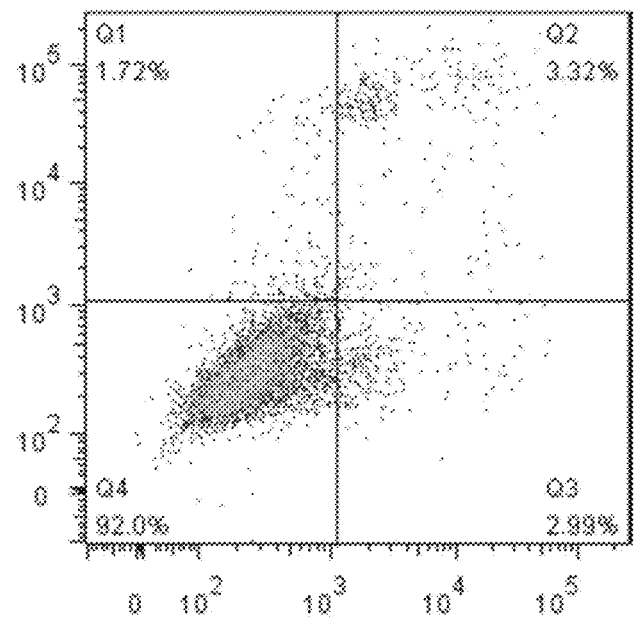
FIGS. 3A, 3B, 3C, 3D, and 3E show Flow Cytometry patterns of H1975 cells having been treated with different concentrations of the compound of Formula (IIa) and of the control group.
Figure 3B:
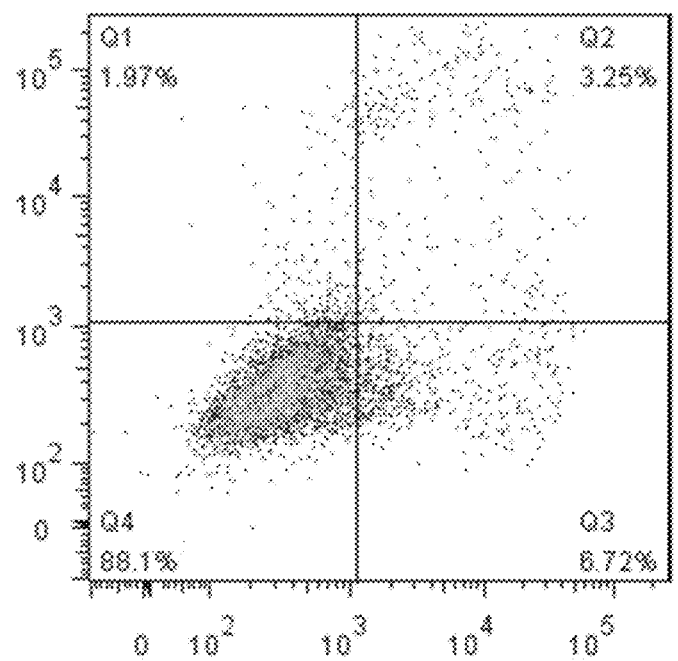
Figure 3C:
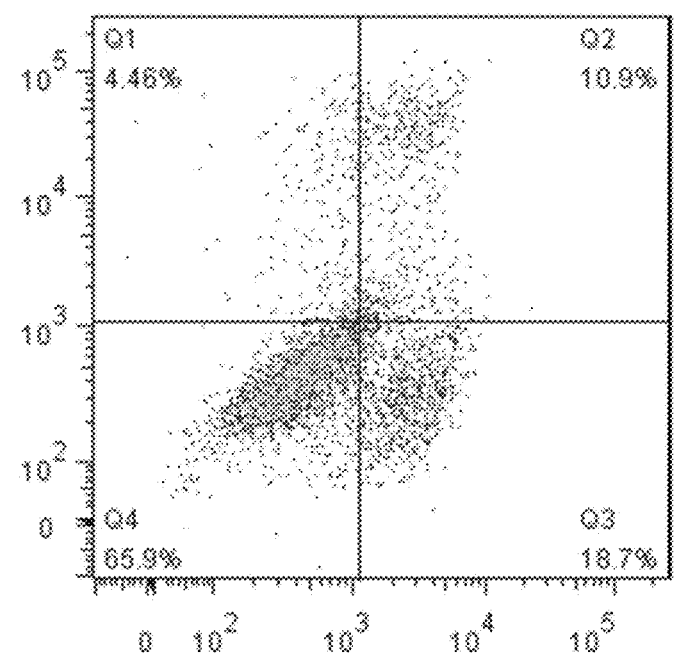
Figure 3D:
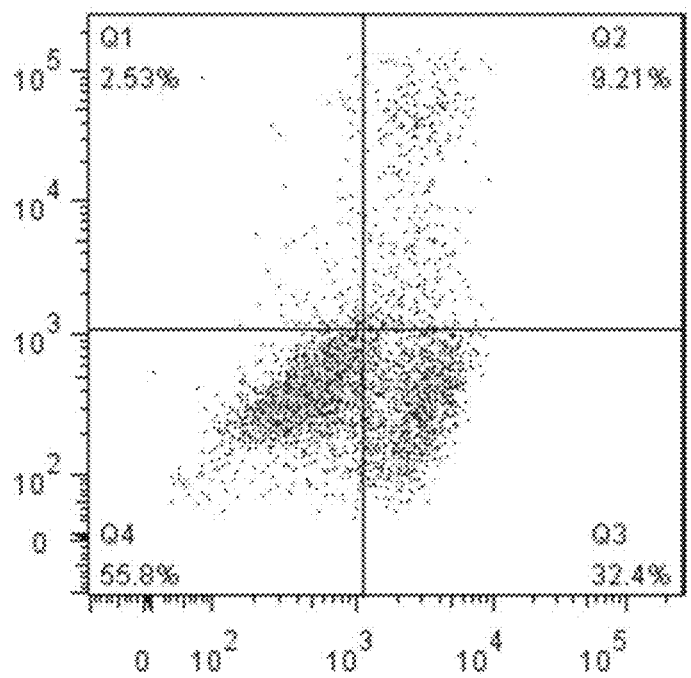
Figure 3E:
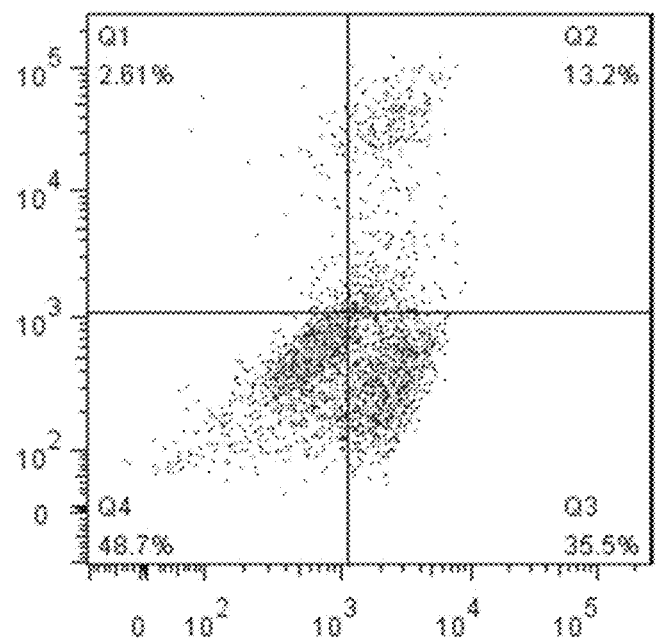
Figure 3F:
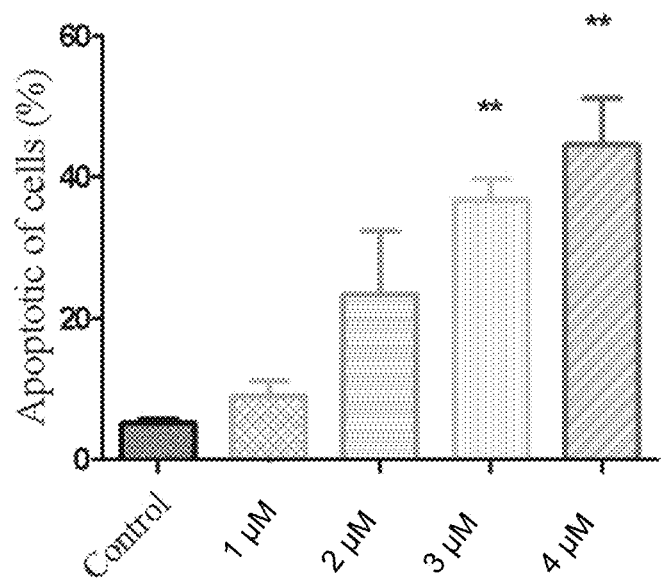
FIG. 3F shows the rate of apoptosis of H1975 cells having been treated with 1 µM, 2 µM, 3 µM or 4 µM of the compound of Formula (IIa) of the present invention compared to the control group.
Figure 4A:
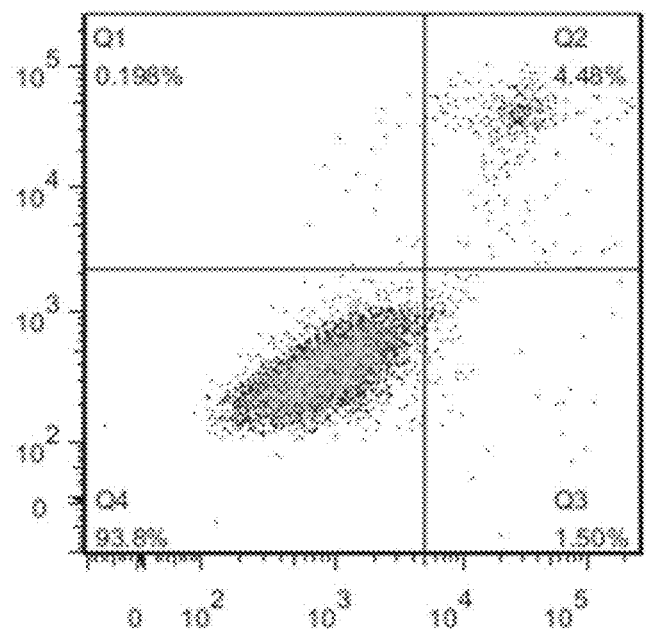
FIGS. 4A, 4B, 4C, and 4D show Flow Cytometry patterns of H1650 cells having been treated with 4 µM of compound of Formula (IIa) in the presence or absence of N-acetylcystein (NAC) compared to treatment with NAC and the control group.
Figure 4B:
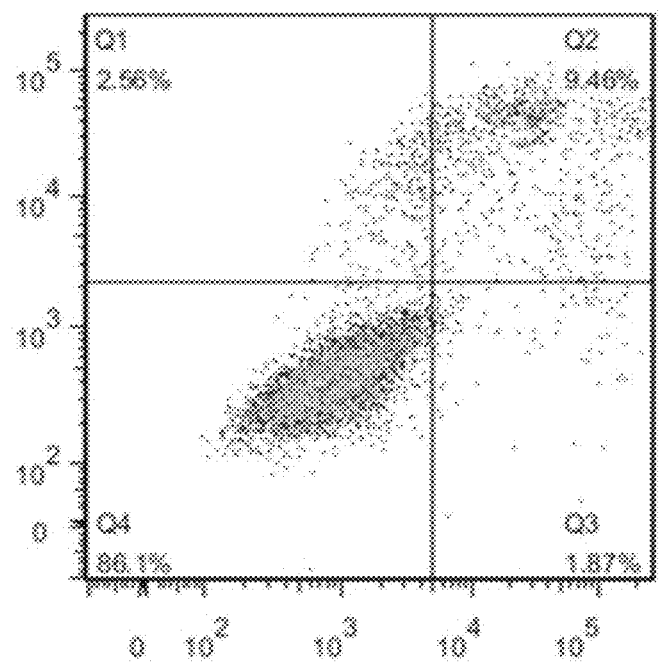
Figure 4C:
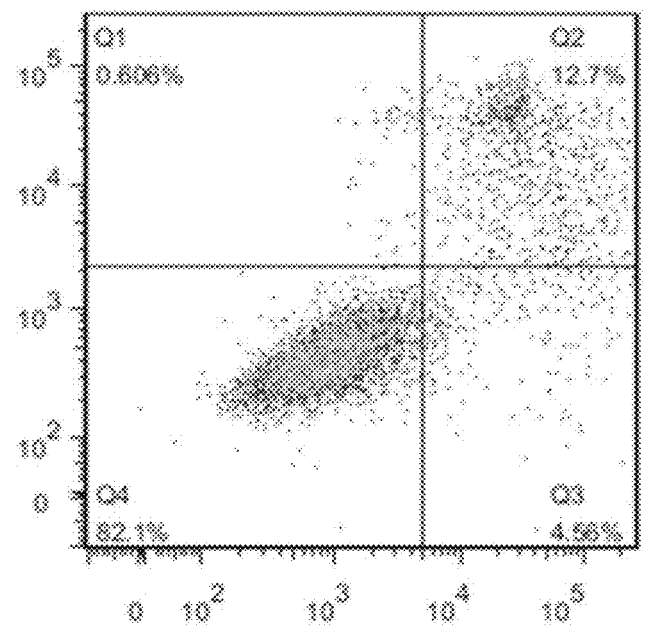
Figure 4D:
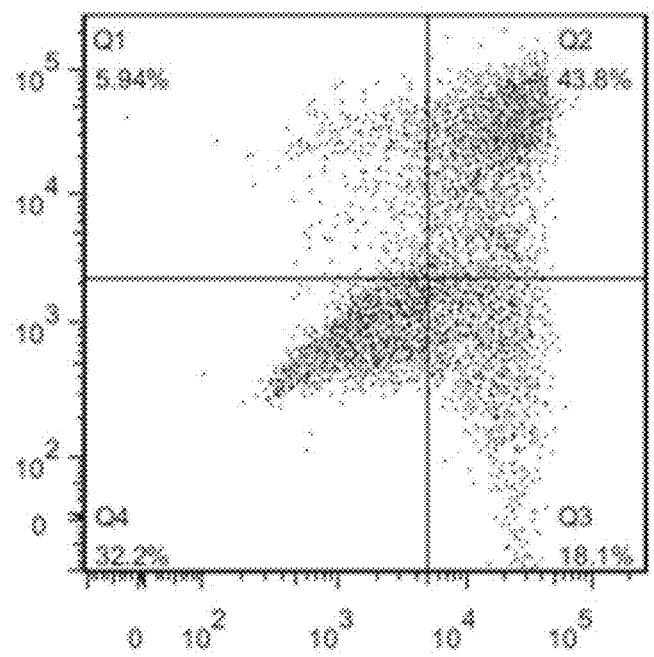
Figure 4E:
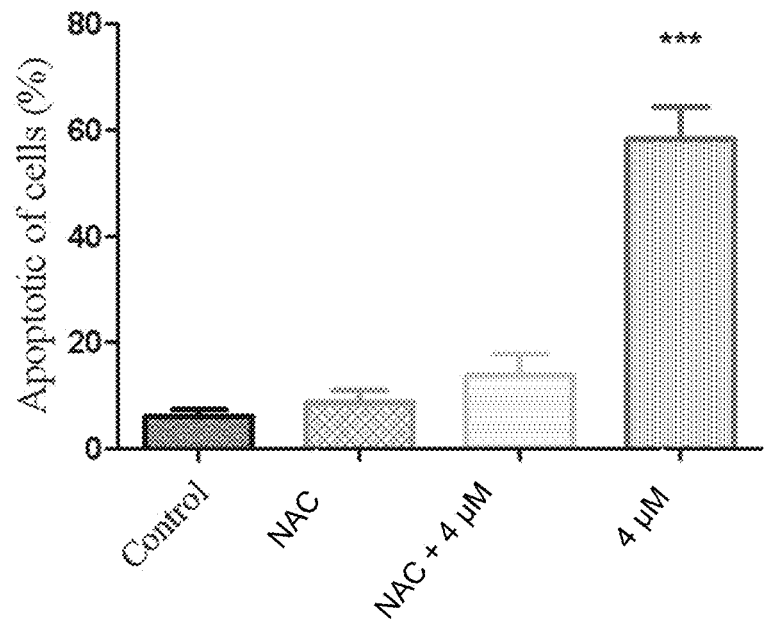
FIG. 4E shows the rate of apoptosis of H1650 cells having been treated with 4 µM of the compound of Formula (IIa) in the presence or absence of NAC compared to the control group.
Figure 5A:
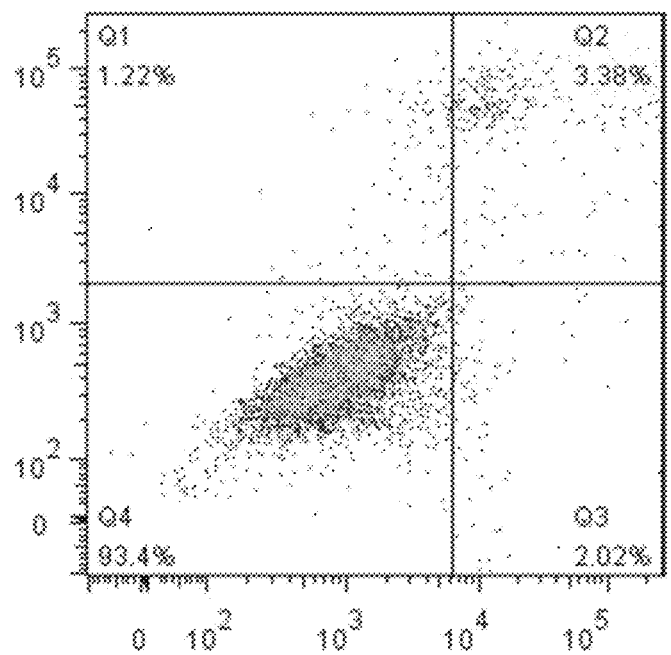
FIGS. 5A, 5B, 5C, and 5D show Flow Cytometry patterns of H1975 cells having been treated with 4 µM of compound of Formula (IIa) in the presence or absence of N-acetylcystein (NAC) compared to treatment with NAC and the control group.
Figure 5B:
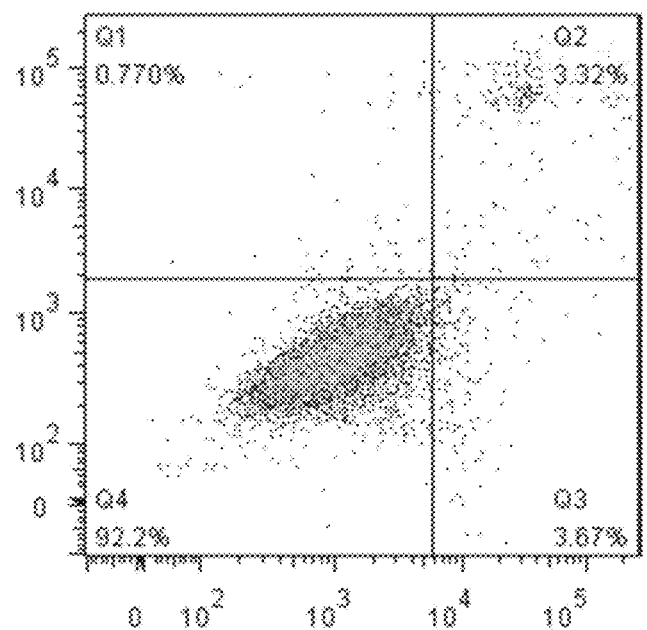
Figure 5C:
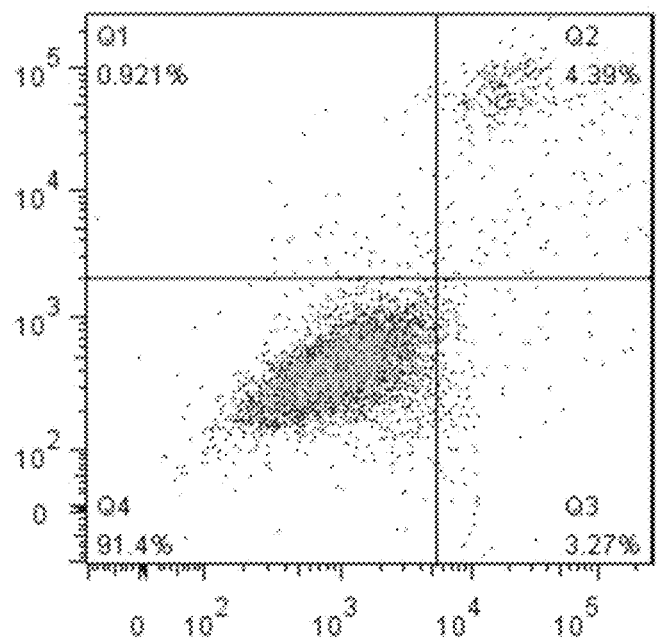
Figure 5D:
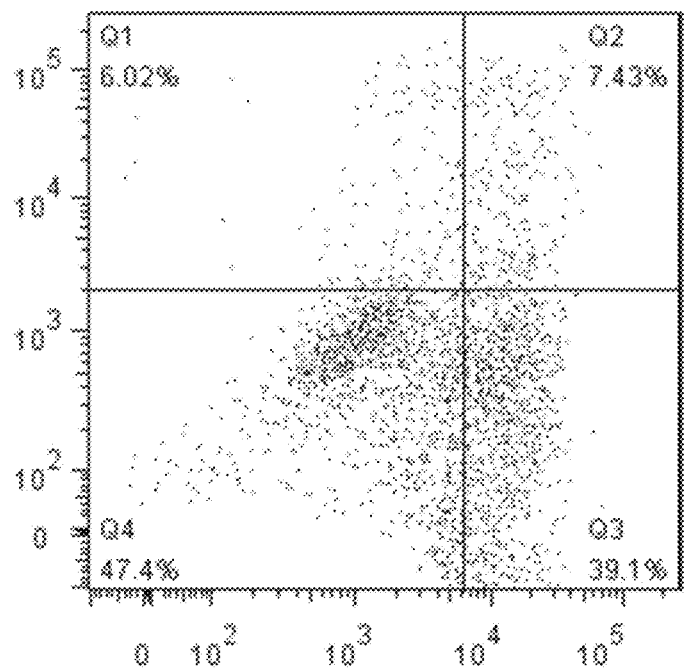
Figure 5E:
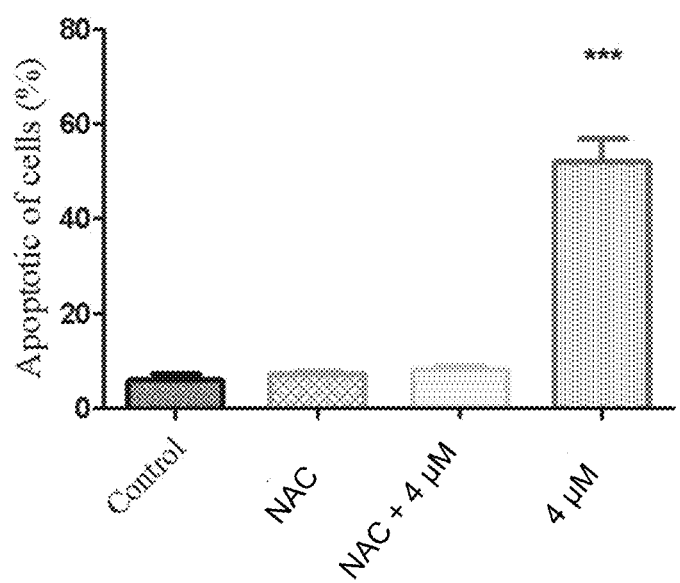
FIG. 5E shows the rate of apoptosis of H1975 cells having been treated with 4 µM of the compound of Formula (IIa) in the presence or absence of NAC compared to the control group.

The following preparations and examples are given to enable those skilled in the art to more clearly understand and to practice the present invention. They should not be considered as limiting the scope of the invention, but merely as being illustrative and for representing preferred embodiments thereof. Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

The technical terms used in the present patent application have the meaning as commonly understood by a respective skilled person unless specifically defined otherwise.

As used herein, "comprising" means including the following elements but not excluding others. "Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element.

The present invention provides a hydroxynaphthoquinone compound for use in a method for treating EGFR-dependent NSCLC in a subject in need thereof. More specifically, the present invention, in a first aspect, refers to a method of treating a subject suffering from EGFR-dependent NSCLC comprising administering an effective amount of a hydroxynaphthoquinone compound to the subject. The cancer is, in particular, an adenocarcinoma.

The term "EGFR-dependent" (or EGFR-positive) as used within this patent application refers to a cancer comprising cancer cells harboring an abnormality in the EGFR gene. An abnormality in the EGFR gene results from a mutation such as due to a substitution, in particular missense substitution, insertion or deletion within the exons 18 to 21 encoding a portion of the EGFR kinase domain, which usually results in an increased kinase activity of EGFR, leading to hyperactivation of downstream pro-survival signaling pathways. In particular, the mutations comprise at least one of an exon 19 deletion or substitution, exon 20 insertion or substitution and/or an exon 21 substitution, in particular at least one of exon 19 deletion and/or an exon 20 substitution. In more preferred embodiments, the abnormality in EGFR gene means at least one mutation selected from E746-A750del deletion in exon 19, L747S substitution in exon 19, D761Y substitution in exon 19, T790M substitution in exon 20, D770_N771 insertion in exon 20, V769L substitution in exon 20, S7681 substitution in exon 20, T854A substitution in exon 21, L858R substitution in exon 21 and/or A871E substitution in exon 21, in particular at least one mutation selected from E746-A750del in exon 19 and/or T790M substitution in exon 20. In most preferred embodiments, at least two mutations of EGFR gene are present, wherein one of them is a T790M substitution in exon 20.

In a particular embodiment, the mutation comprises at least one mutation of L747S substitution in exon 19, D761Y substitution in exon 19, T790M substitution in exon 20, D770_N771 insertion in exon 20, V769L substitution in exon 20, S7681 substitution in exon 20, T854A substitution in exon 21 and/or A871E substitution in exon 21.

Preferably, the abnormality in EGFR gene is associated with a detectable increase in EGFR kinase activity. An "increased kinase activity" of EGFR kinase means an expression of EGFR or an EGFR kinase activity, which is at least 5% and preferably at least 10% and further preferred at least 30% higher compared to a control group, i.e. non-cancerous cells or cancerous cells without abnormality in the EGFR gene. The skilled person is aware of suitable methods for determining EGFR kinase expression or activity such as with immunosorbent assays like with commercially available kits usually with ELISA-based measurement. EGFR expression can be measured, for example, by flow cytometry, real-time PCR, and Western blotting.

Presence of an EGFR mutation can be confirmed by respective molecular biological methods, wherein several methods are known to the skilled person. Such tests are commonly performed using DNA or RNA collected from biological samples, e.g., tissue biopsies, and can be conducted by a variety of methods including, but not limited to, sequence-specific PCR, direct DNA sequencing, hybridization with allele-specific probes, enzymatic mutation detection, chemical cleavage of mismatches or mass spectrometry. I.e. EGFR-dependent NSCLC is in particular considered for being present, if at least one of the above methods reveals an EGFR mutation.

Preferably, the EGFR-dependent NSCLC has an intrinsic or acquired resistance against at least one EGFR inhibitor, preferably against at least one of gefitinib, erlotinib and/or afatinib, more preferably an intrinsic or acquired resistance at least against gefitinib and/or erlotinib and further preferred at least against gefitinib. This means that the cells with EGFR gene abnormality preferably have an intrinsic or acquired resistance against at least one EGFR inhibitor, most preferably at least against gefitinib.

Such resistance can be caused by or follow from the EGFR mutation as such, for example due to insertions or substitutions in exon 20, in particular due to a T790M substitution in exon 20, so that the EGFR inhibitors cannot provide therapeutic advantages. An acquired resistance can also follow from, for example, MET gene amplification encoding MET receptor tyrosine kinase and/or fibroblast growth factor 2 (FGF2) and FGF receptor 1 (FGFR1) induction, mitogen-activated protein kinase 1 (MAPK1) amplification, mutations in downstream effector proteins to EGFR, epithelial-to-mesenchymal transition and small-cell transformation. The resistance against at least one EGFR inhibitor, in particular at least against erlotinib and/or gefitinib, is preferably caused by at least one of an EGFR mutation, MET gene amplification and/or FGF2 and FGFR1 induction. Such EGFR inhibitor resistance can be detected in a subject, tissue, or cell by administering to a subject, tissue or cell an EGFR inhibitor and determining its activity such as the induction of cell death, the inhibition of the proliferation of cancer cells or the activation of EGFR such as one or more of the phosphorylation of EGFR or its signaling proteins like p-Akt, p-MEK1, p-ERK1/2, p-GSK-3α/β, p-p70S6K, or p-p90RSK compared to a control sample of the same cells or tissue without treatment with the EGFR inhibitor and/or compared to a reference sample, namely cells or tissue of the same cell or tissue type or a subject that do not have EGFR inhibitor resistance. This can be carried out by methods known to the skilled person like phosphoprotein assays, cell viability measurement with MTT assays or Western Blotting or the like.

In particular, a cell, tissue or subject is considered for being resistant against an EGFR inhibitor, if the inhibitory effect of the EGFR inhibitor on the activation of EGFR as measured by means of phosphorylated EGFR or phosphorylated signaling proteins downstream to EGFR is significantly lower compared to the inhibitory effect of the EGFR inhibitor in the reference sample, in particular the inhibitory effect on phosphorylated EGFR or phosphorylated signaling proteins is at least 50% reduced compared to the inhibitory effect of the EGFR inhibitor in the reference sample, in particular no significant effect of the EGFR inhibitor can be seen compared to the control sample. Another example for verifying resistance against EGFR inhibitors are commercially available caspase assays like caspase3/caspase7 luminescent assay determining caspase cleavage and apoptosis, wherein the cell, tissue or subject is resistant against an EGFR inhibitor, if the effects of the EGFR inhibitor on the caspase3/7 activity measured are lower than in the reference sample, preferably at most 50% of the caspase activity compared to the reference sample and in particular if no significant effect on the caspase activity is measured compared to the control sample. In other embodiments, cells are resistant against an EGFR inhibitor, if the $IC_{50}$ value measured by means of an MTT assay on the cells or tissue is at least 5-times, in particular at least 10-times, increased compared to the $IC_{50}$ measured in the reference sample.

The cancer is preferably an adenocarcinoma. The terms "cancer" and "cancerous" refer to or describe a physiological condition in subjects in which a population of cells are characterized by unregulated cell growth. The term "tumor" simply refers to a mass being of benign (generally harmless) or malignant (cancerous) growth.

The method of the present invention comprises administering an effective amount of a compound or a pharmaceutically acceptable salt, solvate or anhydrate thereof to a subject. The subject can be a human or animal, in particular the subject is a mammal and further preferred a human. In preferred embodiments of the present invention, the subject is a mammal, in particular a human, having an abnormality in EGFR gene and with intrinsic or acquired resistance against at least one of gefitinib, erlotinib and/or afatinib, in particular intrinsic or acquired resistance at least against gefitinib and/or erlotinib, which abnormality in EGFR gene includes at least one of an exon 19 deletion or substitution, exon 20 insertion or substitution and/or an exon 21 substitution, in particular at least one of E746-A750del deletion in exon 19, L747S substitution in exon 19, D761Y substitution in exon 19, T790M substitution in exon 20, D770_N771 insertion in exon 20, V769L substitution in exon 20, S7681 substitution in exon 20, T854A substitution in exon 21, L858R substitution in exon 21 and/or A871E substitution in exon 21, more preferably at least one of E746-A750del deletion in exon 19 and/or T790M substitution in exon 20. In a particular embodiment, the mutation comprises at least one of L747S substitution in exon 19, D761Y substitution in exon 19, T790M substitution in exon 20, D770_N771 insertion in exon 20, V769L substitution in exon 20, S7681 substitution in exon 20, T854A substitution in exon 21 and/or A871E substitution in exon 21.

The compound of the present invention is a hydroxynaphthoquinone compound, namely a hydroxy-1,4-naphthoquinone compound, also named hydroxy-4a,8a-dihydronaphthalene-1,4-dione, and more specifically a 4a,8a-dihydro-5,8-dihydroxynaphthalene-1,4-dione compound. Hydroxy-1,4-naphthoquinones are compounds which are, for example, known from plants and microorganism representing secondary metabolites.

The compound of the present invention has a structure of Formula (I) or is any pharmaceutically acceptable salt, anhydrate or solvate thereof:

Formula (I)

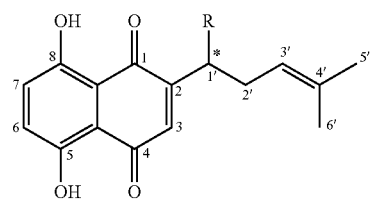

R is selected from H, OH,

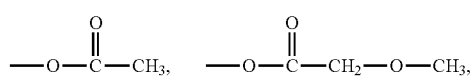

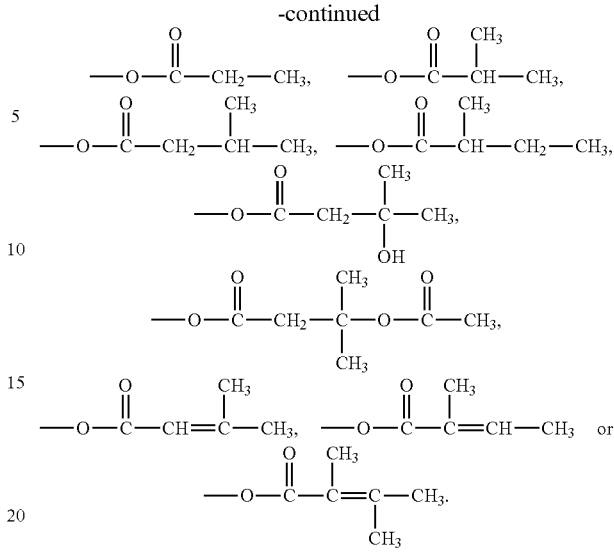

Also contemplated by the present invention are enantiomers and their mixtures and racemates of the compounds of Formula (Ia) and Formula (Ib) comprising a stereogenic carbon atom in position 1'. Namely, Formula (I) includes the enantiomers of Formula (Ia) and (Ib), their mixtures and the racemate:

Formula (Ia)

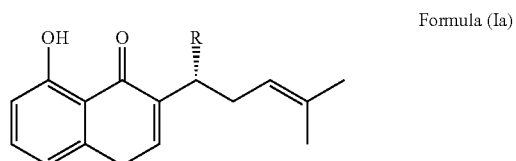

Formula (Ib)

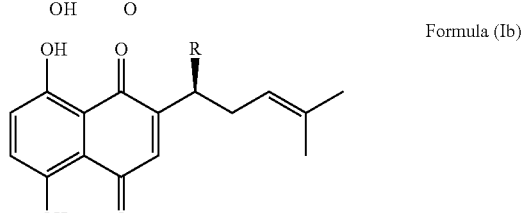

In an embodiment of the present invention, the compound is the enantiomer of Formula (Ia), wherein R is as defined above. In another embodiment of the present invention, the compound is the enantiomer of Formula (Ib), wherein R is as defined above. In still another embodiment of the present invention, the compound is a mixture of the enantiomer of Formula (Ia) and of Formula (Ib) or a racemate thereof, wherein R is as defined above.

The compounds of Formula (I) can be prepared by suitable methods, such as by chemical synthesis, by extraction from plant materials or from suitable cell tissue cultures. Methods for separating enantiomers are known to the skilled person, too, like chiral chromatography. The compound of Formula (I), is, for example, obtainable from plants of the Boraginaceae family such as, for example, from the *Arnebia* genus, *Alkanna* genus or *Lithospermum* genus and including, for example, *Arnebia euchroma, Arnebia guttata, Arnebia hispidissima, Arnebia nobilis, Arnebia tinctoria, Arnebia densiflora, Alkanna tinctoria, Lithospermum* arvense or Lithospermum erythrorhizon. The compound of Formula (I) can in particular be isolated from the roots of the above-mentioned plants, more preferably from the roots of Lithospermum erythrorhizon. Methods for extraction can include steps of:

Optionally drying the plant material, and/or cutting, shredding, milling and/or pulverizing the plant material;

Subjecting the plant material to a solvent extraction with an extraction solvent, for example by utilizing a Soxhlet extractor, which extraction solvent can be, for example, an alkane line n-hexane or petroleum ether, a halogenated alkane like dichloromethane or chloroform, an ester like ethyl acetate or an alcohol like methanol or mixtures thereof;

Removing the extraction solvent for obtaining a crude extract; and

Optionally separating compounds from the crude extract and purifying the compounds.

As used herein, the term "solvate" refers to a complex of variable stoichiometry formed by a solute, i.e. compound of Formula (I), and a solvent. If the solvent is water, the solvate formed is a hydrate. As used herein, the term "anhydrate" means any compound free of the water of hydration, as would be understood in the art. Suitable pharmaceutically acceptable salts are those which are suitable to be administered to subjects, in particular mammals such as humans and can be prepared with sufficient purity and used to prepare a pharmaceutical composition. The terms enantiomers and racemates are known to the skilled person.

In especially preferred embodiments, the compound is a compound of Formula (II):

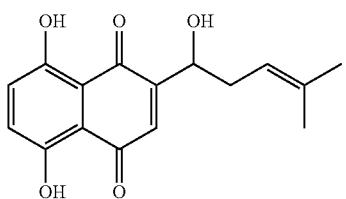

Formula (II)

The compound includes the enantiomers, their mixtures or is a racemate of the compounds of Formula (IIa) and (IIb):

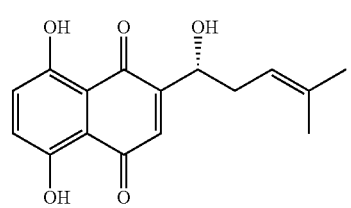

Formula (IIa)

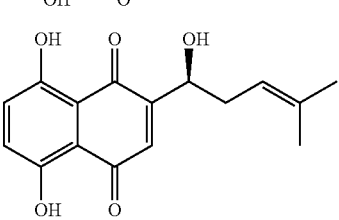

Formula (IIb)

In one preferred embodiment, the compound is a compound of Formula (IIa) or any pharmaceutically acceptable salt, solvate or anhydrate thereof, which compound is also named shikonin and represents the R-enantiomer. In alternative embodiments, the compound is a compound of Formula (IIb), or any pharmaceutically acceptable salt, solvate or anhydrate thereof, also named alkannin representing the S-enantiomer.

The inventors conclude that the compound of Formula (I), in particular the compound of Formula (IIa), is especially suitable to inhibit EGFR kinase activity in EGFR-dependent NSCLC in particular with intrinsic or acquired resistance against EGFR inhibitors. Said compound is suitable to induce apoptosis accompanied by an enhanced generation of oxidative reactive species (ROS), too, in EGFR-dependent NSCLC. Such interactions are able to allow for sufficiently and exceptionally inhibiting the EGFR transautophosphorylation and anti-apoptotic and growth signaling downstream to EGFR.

As further shown below, respective data with EGFR-dependent adenocarcinoma cell lines with gefitinib resistance further confirm that compound of Formula (IIa) is especially effective in inhibiting EGFR kinase activity. The compound of Formula (IIa) proved to be highly cytotoxic and selective to NSCLC cells. In particular, the compound of Formula (IIa) proved to exceptionally induce apoptosis and suppress the transautophosphorylation of EGFR kinase while making use of EGFR-dependent NSCLC cell lines with gefitinib resistance.

The expression "effective amount" generally denotes an amount sufficient to produce therapeutically desirable results, wherein the exact nature of the result varies depending on the specific disorder which is treated. When the disorder is cancer, the result is usually an inhibition or suppression of the proliferation of the cancer cells, a reduction of cancerous cells or the amelioration of symptoms related to the cancer cells, in particular inhibition, reduction or prevention of the proliferation of the cancer cells or induction of cell death, i.e. apoptosis of the cancer cells.

The effective amount of the compound of Formula (I) may depend on the species, body weight, age and individual conditions and can be determined by standard procedures such as with cell cultures or experimental animals. The concentration of the compound of Formula (I), such as the compound of Formula (IIa), effective for treating the subject may, for example, be at least 1 μM, preferably at least 2 μM, in particular at least 3 μM and further preferred at least 4 μM.

The compound of Formula (I) has an $IC_{50}$ on EGFR-dependent NSCLC cells of at most 10 μM, preferably at most 5 μM and in particular at most 4 μM and an $IC_{50}$ on non-cancerous lung cells being at least 2 times higher, more preferably 3 times higher than the $IC_{50}$ on EGFR-dependent NSCLC cells.

In embodiments of the present invention, the disease is EGFR-dependent NSCLC with intrinsic or acquired resistance at least against one of gefitinib, erlotinib and/or afatinib, in particular at least against gefitinib and/or erlotinib, and the compound has an $IC_{50}$ on said NSCLC cells of at most 5 μM and an $IC_{50}$ on non-cancerous lung cells being at least 2 times higher, preferably at least 3 times higher than the $IC_{50}$ on the NSCLC cells harboring an abnormality in the EGFR gene.

The method of the present invention may further include steps carried out before administering the compound of Formula (I), such as compound of Formula (IIa), to the subject comprising:

Obtaining a sample, in particular cancer cells, from the subject;

Testing said sample for the EGFR kinase activity and/or identifying at least one EGFR mutation as abnormality in the EGFR gene;

Optionally correlating the EGFR kinase activity and/or abnormality in the EGFR gene with outcome and if conditions are met, administrating the compound of Formula (I), in particular compound of Formula (IIa), to said subject.

According to the invention is also the compound of Formula (I), in particular the compound of Formula (IIa), for use in the treatment of EGFR-dependent NSCLC, in particular EGFR-dependent NSCLC with intrinsic or acquired resistance against an EGFR inhibitor such as selected from at least one of gefitinib, erlotinib and/or afatinib, in particular with intrinsic or acquired resistance at least against gefitinib and/or erlotinib. The compound of Formula (I), in particular the compound of Formula (IIa), can be used in an effective amount for treating a human. Another aspect of the invention refers to the use of the compound of Formula (I), in particular the compound of Formula (IIa), for preparing a medicament for treatment of EGFR-dependent NSCLC, in particular EGFR-dependent NSCLC with intrinsic or acquired resistance against an EGFR inhibitor such as selected from at least one of gefitinib, erlotinib and/or afatinib, in particular with intrinsic or acquired resistance at least against gefitinib and/or erlotinib.

The compound of Formula (I) may be used in combination with other therapeutic compounds, preferably therapeutic compounds which are used for treating NSCLC.

In still another aspect, the present invention refers to a method of inhibiting EGFR kinase activity in NSCLC cells harboring an abnormality in the EGFR gene by a compound of Formula (I), i.e. comprising administering an effective amount of the compound of Formula (I) or a pharmaceutically acceptable salt, solvate or anhydrate thereof:

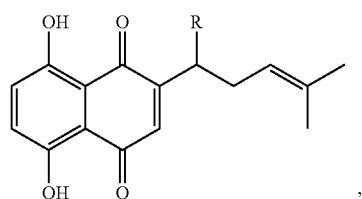

Formula (I)

R is selected from H, OH,

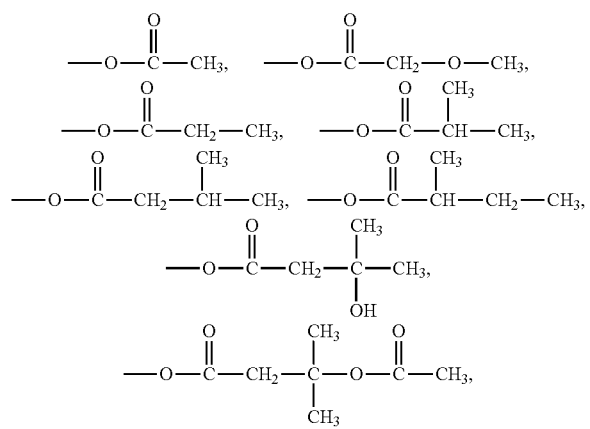

-continued

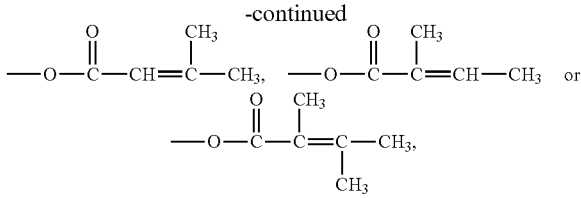

to a subject suffering from EGFR-dependent NSCLC.

The compound, in particular, is a compound of Formula (II), more preferably of Formula (IIa):

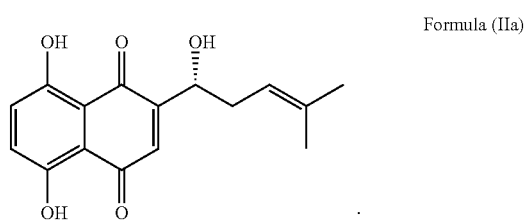

Formula (IIa)

The EGFR-dependent NSCLC is in particular EGFR-dependent NSCLC with intrinsic or acquired resistance against at least one EGFR inhibitor such as selected from at least one of gefitinib, erlotinib and/or afatinib, further preferred intrinsic or acquired resistance at least against gefitinib and/or erlotinib. In one embodiment of the present invention, the disease is an adenocarcinoma. This means that the NSCLC cells harboring an abnormality in the EGFR gene, in particular have an intrinsic or acquired resistance against at least one EGFR inhibitor.

The subject can be a human or animal, in particular the subject is a mammal and further preferred a human. The abnormality in EGFR gene preferably means at least one of an exon 19 deletion or substitution, exon 20 insertion or substitution and/or an exon 21 substitution, in particular at least one of E746-A750del deletion in exon 19, L747S substitution in exon 19, D761Y substitution in exon 19, T790M substitution in exon 20, D770_N771 insertion in exon 20, V769L substitution in exon 20, S7681 substitution in exon 20, T854A substitution in exon 21, L858R substitution in exon 21 and/or A871E substitution in exon 21, more preferably at least one of E746-A750del deletion in exon 19 and/or T790M substitution in exon 20. In a particular embodiment, the abnormality in the EGFR gene means at least one of L747S substitution in exon 19, D761Y substitution in exon 19, T790M substitution in exon 20, D770_N771 insertion in exon 20, V769L substitution in exon 20, S7681 substitution in exon 20, T854A substitution in exon 21 and/or A871E substitution in exon 21.

The compound of Formula (I) has an $IC_{50}$ on the NSCLC cells with the abnormality in the EGFR gene of at most 10 μM, preferably at most 5 μM and in particular at most 4 μM and an $IC_{50}$ on non-cancerous lung cells being at least 2 times higher, more preferably 3 times higher than the $IC_{50}$ on the NSCLC cells.

The compound of the present invention may be administered in the methods of the present invention described above in form of a composition comprising the compound of Formula (I), in particular the compound of Formula (IIa), or a salt, solvate or anhydrate thereof. The composition further comprises excipients such as pharmaceutically acceptable excipients, a buffer, salt, water or a combination thereof. In particular the composition is a pharmaceutical composition comprising the compound of Formula (I), in particular the compound of Formula (IIa), or a pharmaceutically acceptable salt, solvate or anhydrate thereof. Said pharmaceutical composition further comprises pharmaceutically acceptable excipients and may additionally contain further active ingredients, in particular therapeutic compounds for treating NSCLC.

The skilled person is able to select suitable excipients depending on the form of the pharmaceutical composition and is aware of methods for manufacturing pharmaceutical compositions as well as able to select a suitable method for preparing the pharmaceutical composition depending on the kind of excipients and the form of the pharmaceutical composition. The pharmaceutical composition according to the invention can be present in solid, semisolid or liquid form to be administered by an oral, rectal, topical, parenteral or transdermal or inhalative route to a subject, preferably a human.

Preferably, the pharmaceutically acceptable excipient is at least one of a diluent, a filler, a binder, a disintegrant, a lubricant, a coloring agent, a surfactant or a preservative. The present invention also refers to the use of the composition such as the pharmaceutical composition for inhibiting EGFR kinase activity in subjects with EGFR-dependent cancer and/or NSCLC cells harboring an abnormality in the EGFR gene, in particular EGFR-dependent NSCLC and NSCLC cells with an abnormality in the EGFR gene, respectively, and with intrinsic or acquired resistance against EGFR inhibitors such as selected from at least one of gefitinib, erlotinib and/or afatinib, in particular with intrinsic or acquired resistance at least against gefitinib and/or erlotinib.

The present invention in another aspect refers to a method for targeting NSCLC cells harboring an abnormality in EGFR gene comprising the step of contacting said cells with a hydroxynaphthoquinone compound of Formula (I) or a salt, solvate or anhydrate thereof:

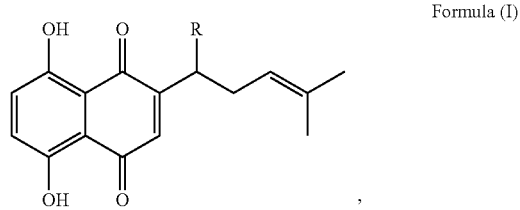

Formula (I)

R is selected from H, OH,

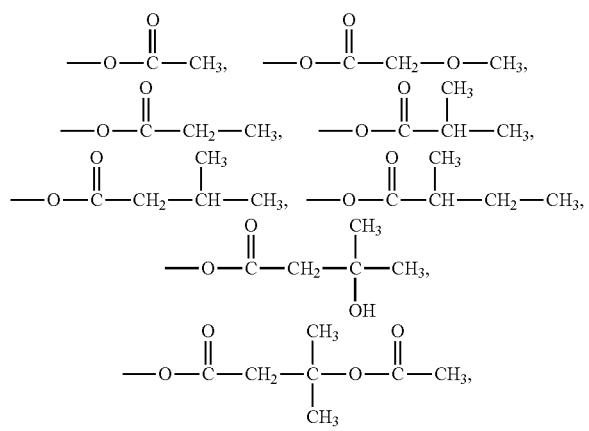

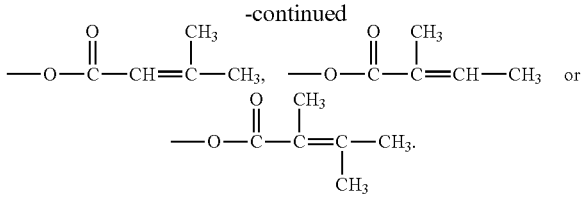

The abnormality in EGFR gene, in particular, includes at least one of an exon 19 deletion or substitution, exon 20 insertion or substitution and/or an exon 21 substitution, in particular at least one of E746-A750del deletion in exon 19, L747S substitution in exon 19, D761Y substitution in exon 19, T790M substitution in exon 20, D770_N771 insertion in exon 20, V769L substitution in exon 20, S7681 substitution in exon 20, T854A substitution in exon 21, L858R substitution in exon 21 and/or A871E substitution in exon 21, more preferably at least one of E746-A750del deletion in exon 19 and/or T790M substitution in exon 20. In a particular embodiment, the mutation comprises at least one of L747S substitution in exon 19, D761Y substitution in exon 19, T790M substitution in exon 20, D770_N771 insertion in exon 20, V769L substitution in exon 20, S7681 substitution in exon 20, T854A substitution in exon 21 and/or A871E substitution in exon 21. More preferably, the NSCLC cells harboring an abnormality in the EGFR gene have an intrinsic or acquired resistance against at least one of gefitinib, erlotinib and/or afatinib, in particular at least against gefitinib and/or erlotinib. The EGFR-dependent NSCLC cells are preferably from an adenocarcinoma.

Preferably, the proliferation of the NSCLC cells is inhibited, reduced or prevented or apoptosis of the cancer cells is induced, more preferably apoptosis of the NSCLC cells is induced. The skilled person is aware of methods for verifying such effects such as with cell viability measurement by means of a MTS proliferation assay, a MTT assay, Caspase-3 assay or by determination of the apoptosis rate by means of Annexin V flow cytometry measurement.

Preferably, the NSCLC cells are contacted with the compound of Formula (I) for at least 10 h, more preferably for at least 12 h such as for about 24 h. The compound of Formula (I) is preferably used for contacting the cells in a concentration of at least 1 µM, more preferably of at least 2 µM and especially preferably at least 3 µM and further preferred of at least 4 µM. The NSCLC cells contacted with the compound of Formula (I) may comprise between 1.0× $10^3$ cells and 1.0×$10^6$ cells, in particular about 1.0×$10^6$ cells.

The compound of Formula (I) has an $IC_{50}$ on the NSCLC cells harboring an abnormality in the EGFR gene of at most 10 µM and an $IC_{50}$ on non-cancerous lung cells being at least 2 times higher, preferably at least 3 times higher than the $IC_{50}$ on said NSCLC cells.

In embodiments of the present invention, the abnormality in EGFR gene in particular includes at least one of E746-A750del deletion in exon 19 and/or T790M substitution in exon 20, and the compound has an $IC_{50}$ on the NSCLC cells harboring an abnormality in the EGFR gene of at most 5 µM and an $IC_{50}$ on non-cancerous lung cells being at least 3 times higher than the $IC_{50}$ on said NSCLC cells. More preferably, the NSCLC cells harboring an abnormality in the EGFR gene have an intrinsic or acquired resistance against at least one of gefitinib, erlotinib and/or afatinib, in particular against at least gefitinib and/or erlotinib. The NSCLC cells harboring an abnormality in the EGFR gene are preferably from an adenocarcinoma.

Still more preferably, the compound used for contacting said NSCLC cells harboring an abnormality in the EGFR gene is a compound having Formula (II) or a salt, solvate or anhydrate thereof:

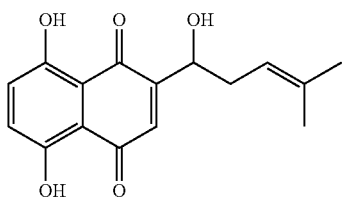

Formula (II)

and is in particular used in a concentration of at least 2 µM.

Especially preferably, the compound used for contacting the NSCLC cells harboring an abnormality in the EGFR gene is a compound having Formula (IIa):

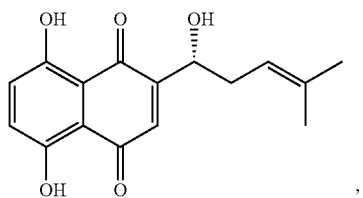

Formula (IIa)

wherein the concentration of compound (IIa) for contacting said cells is at least 2 µM, in particular at least 3 µM and further preferred at least 4 µM, wherein the cells are preferably contacted with the compound for at least 12 h.

EXAMPLES

The efficiency of the compound of Formula (IIa) as inhibitor of EGFR has been evaluated. First of all, the cytotoxic properties of the compound of Formula (IIa) with regard to cells with abnormality in the EGFR gene have been analyzed. Secondly, the induction of apoptosis has been evaluated and the effects on the EGFR phosphorylation and anti-apoptotic and growth signaling pathways downstream to EGFR.

In the below examples, differences are analyzed by one-way ANOVA. All statistical analyses are carried out using Graph Prim5.0. Values of P<0.05 were considered statistically significant.

Example 1

Cytotoxicity of the Compound of Formula (IIa) on NSCLC Cells with Abnormality in the EGFR Gene and Non-Cancerous Lung Epithelial Cells To show the highly cytotoxic properties of the present compound of Formula (IIa), H1650, HCC827 and H1975 NSCLC cells and non-cancerous lung fibroblast cells (CCD-19LU) were treated with the compound of Formula (IIa) and respective effects were observed. H1650 cells are adenocarcinoma cells harboring an E746-A750del deletion in exon 19 and other driver mutation genes which lead to a resistance against gefitinib. HCC827 cells are adenocarcinoma cells harboring high level EGFR amplification and an E746-A750del deletion in exon 19 without gefitinib-resistance. H1975 cells are adenocarcinoma cells harboring L858R substitution in exon 21 and a T790M substitution in exon 20 which is directly associated with resistance against gefitinib. The cells were obtained from the American Type Culture Collection (ATCC) and cultured in environment of 5% $CO_2$ at 37° C. in RPMI-1640 medium supplemented with 10% fetal bovine serum (FBS), 100 units/mL penicillin, and 100 µg/mL streptomycin. The compound of Formula (IIa) was dissolved in DMSO. Using a MTT assay, 4000 cells/well of an adenocarcinoma cell type or CCD-19LU cells were seeded on 96-well plates, cultured overnight for cell adhesion, and treated with DMSO or various concentrations of the compound of Formula (IIa) for 24 h. Three independent tests were performed. 10 µL of MTT (5 mg/mL; Sigma) were added to each well, and incubation continued for another 4 h. Then the dark blue crystals were dissolved in 100 µL of the resolved solution (10% SDS and 0.1 mM HCL). The absorbance was measured at 570 nm by a microplate reader (Tecan, Morrisville, N.C., USA).

The cell viability was calculated relative to untreated controls, with results based on at least three independent experiments. The MTT assay confirmed that the compound of Formula (IIa) shows selectively cytotoxic effects on NSCLC cells harboring an abnormality in the EGFR gene with $IC_{50}$ values given in table 1 while it shows much lower cytotoxicity on non-cancerous lung fibroblast cells (CCD-19LU) after 24 h treatment (FIG. 1A to FIG. 1D and table 1). The compound of Formula (IIa), thus, proved to be highly selectively towards the NSCLC cells.

TABLE 1

| $IC_{50}$ of the compound of Formula (IIa) | |
|---|---|
| Cell lines | $IC_{50}$ (µM) |
| H1650 | 3.849 µM ± 0.354 |
| HCC827 | 3.511 µM ± 0.375 |
| H1975 | 2.635 µM ± 0.192 |
| CCD-19LU | 12.16 µM ± 1.00 |

Example 1B

Anticancer Effect of the Compound of Formula (IIa) Through Inducing Apoptosis in Gefitinib-Resistant NSCLC Cells with Abnormality in the EGFR Gene Apoptosis assay was performed on gefitinib-resistant H1650 and H1975 cells. The cells ($1.0 \times 10^5$ cells/well) were allowed to attach to a 6-well plate for 24 h, and the cells were treated with the various concentrations of the compound of Formula (IIa) for additional 24 h. At the end of incubation, the cells were harvested by trypsinization and washed twice with ice-cold PBS. After centrifugation and removal of the supernatants, cell pellets were resuspended in 100 µL 1×Annexin-binding buffer, 2 µL Annexin-V FITC and 2 µL PI (100 µg/ml) were added and incubated in the dark at room temperature for 15 min before further addition of 400 µL of 1×Annexin-binding buffer. The stained cells were analyzed quantitatively using a flow cytometer (BD Biosciences, San Jose, Calif., USA). Data were analyzed by Flow Jo software.

FIG. 2A to 2E show fluorescence images of H1650 cells and FIG. 3A to 3E show fluorescence images of H1975 cells having been treated with the compound of Formula (IIa) at 1 µM, 2 µM, 3 µM and 4 µM; and DMSO (control, negative control).

It is evident, that the compound of Formula (IIa) significantly induced apoptosis of the gefitinib-resistant NSCLC cells in a concentration-dependent manner.

Example 1C

Compound of Formula (IIa) Enhances Reactive Oxygen Species (ROS) Generation in Gefitinib-Resistant NSCLC Cells with Abnormality in the EGFR Gene Apoptosis assay and analysis with flow cytometer was performed as described in Example 1B with H1650 and H1975 cells and treatment with 4 µM of the compound of Formula (IIa) for 30 min in the presence or absence of N-acetylcystein (NAC) or treatment with DMSO (control, negative control). FIG. 4A to 4D show fluorescence images of H1650 cells and FIG. 5A to 5D show fluorescence images of H1975 cells.

ROS generation was considered as the direct cause of apoptosis induced by the compound of Formula (IIa). After 30 min treatment of the H1650 and H1975 cells, the intensity of ROS increased more than 10-fold. NAC, an inhibitor of ROS, completely blocked the apoptosis induced by the compound of Formula (IIa).

Example 1D

Compound of Formula (IIa) Leads to a Reduced Caspase and PARP Activation in Gefitinib-Resistant NSCLC Cells with Abnormality in the EGFR Gene The H1650 or H1975 cells were planted on 6-well plates, allowed to attach for 24 h, and treated with 4 µM of the compound of Formula (IIa) with or without NAC (10 mM) for 24 h. Cells were washed twice with cold PBS then lysed in RIPA lysis buffer containing protease and phosphatase inhibitors. Protein concentration of the cell lysates was measured using the Bio-Rad protein Assay kit (Bio-Rad, 7 Philadelphia, Pa., USA). After equalizing the protein concentrations of the samples, 5× laemmli buffer was added and the samples were boiled at 100° C. for 5 min. Equal amounts of protein samples (30 µg) were subjected to SDS-PAGE of a 10% gel. The separated proteins were transferred to a nitrocellulose (NC) membrane, which was then exposed to 5% non-fat dried milk in TBS containing 0.1% Tween (0.1% TBST) for 1 h at room temperature, followed by overnight incubation at 4° C. with primary antibodies. After washing three times by TBST (5 mins/time), the membranes were incubated for 1 h at room temperature with secondary fluorescent antibodies (1:10000 dilutions) to rabbit or mouse. The signal intensity of the membranes was detected by an LI-COR Odessy scanner (Belfast, Me., USA).

Figure 6:
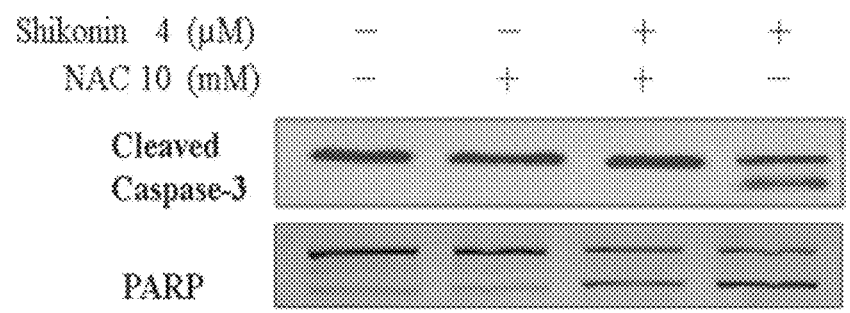
FIG. 6 refers to a western blot and shows the expression of cleaved caspase-3 and cleaved PARP being indicators of apoptosis, wherein a control group and H1650 cells treated with 4 µM of the compound of Formula (IIa) for 24 h with or without 10 mM NAC are shown.
Figure 7:
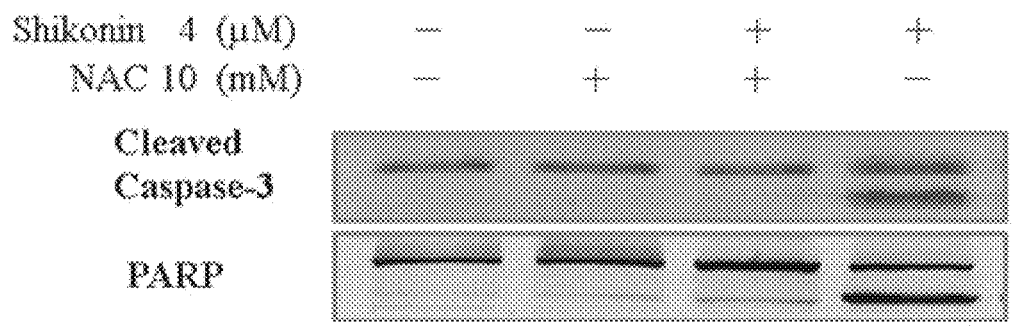
FIG. 7 refers to a western blot and shows the expression of cleaved caspase-3 and cleaved PARP being indicators of apoptosis, wherein a control group and H1975 cells treated with 4 µM of the compound of Formula (IIa) for 24 h with or without 10 mM NAC are shown.

As illustrated in FIG. 6 and FIG. 7, the compound of Formula (IIa) lead to an increased apoptosis indicated by the increase in cleaved Caspase-3 and cleaved Poly(ADP-ribose) Polymerase (PARP) as downstream effector to caspases. As evident, the apoptosis was blocked by NAC.

Example 1E

Suppression of EGFR Phosphorylation Signaling Pathways by the Compound of Formula (IIa) in Gefitinib-Resistant NSCLC Cells with Abnormality in the EGFR Gene H1975 cells were planted on 6-well plate, allowed to attach for 24 h, and treated with the various concentrations of the compound of Formula (Ic) for 2 h. Cells were washed twice with cold PBS then lysed in RIPA lysis buffer containing protease and phosphatase inhibitors. Protein concentration of the cell lysates was measured using the Bio-Rad protein Assay kit (Bio-Rad, 7 Philadelphia, Pa., USA). After equalizing the protein concentrations of the samples, 5× laemmli buffer was added and the samples were boiled at 100° C. for 5 min. Equal amounts of protein samples (30 µg) were subjected to SDS-PAGE of a 10% gel. The separated proteins were transferred to a nitrocellulose (NC) membrane, which was then exposed to 5% non-fat dried milk in TBS containing 0.1% Tween (0.1% TBST) for 1 h at room temperature, followed by overnight incubation at 4° C. with primary antibodies. After washing three times by TBST (5 mins/time), the membranes were incubated for 1 h at room temperature with the secondary fluorescent antibodies (1:10000 dilutions) to rabbit or mouse. The signal intensity of the membranes was detected by an LI-COR Odessy scanner (Belfast, Me., USA). Actin was used as the loading control for normalization.

Figure 8:
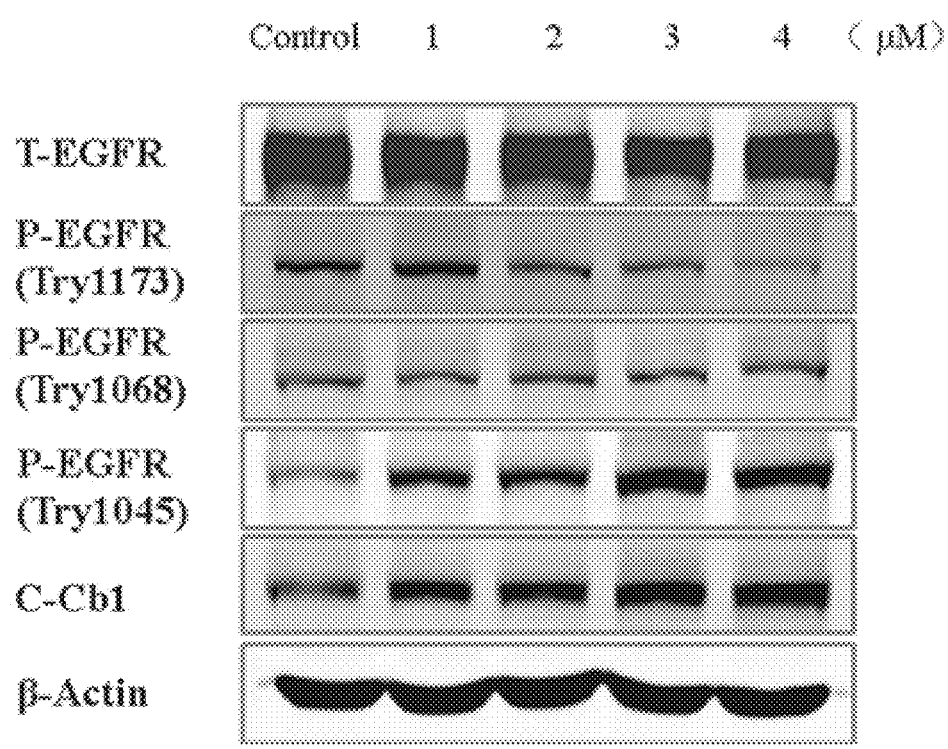
FIG. 8 refers to a western blot and shows the expression of EGFR, phosphorylated EGFR as activated form of EGFR (tyrosine phosphorylation sites 1068 and 1173 related with EGFR activation, and tyrosine 1045 associated with EGFR degradation) and c-Cbl assumed to downregulate EGFR expression, wherein a control group and H1975 cells treated with 1 µM, 2 µM, 3 µM and 4 µM of the compound of Formula (IIa) are shown.

The compound of Formula (IIa) proved to suppress EGFR phosphorylation and anti-apoptotic and growth signaling pathways that are downstream to EGFR. This is evident from the results for the tyrosine phosphorylation site 1068 and 1173 related with EGFR activation, and for tyrosine 1045 associated with EGFR degradation. C-Cb1 is related to degradation of EGFR, either. The results illustrated in FIG. 8, thus, prove that the compound of Formula (IIa) inhibits EGFR a, its transautophosphorylation and, thus, signaling pathways downstream to EGFR.

The invention claimed is:

1. A method of treating a subject suffering from EGFR-dependent non-small cell lung cancer comprising administering an effective amount of a hydroxynaphthoquinone compound of Formula (I) or a pharmaceutically acceptable salt, solvate or anhydrate thereof to the subject:

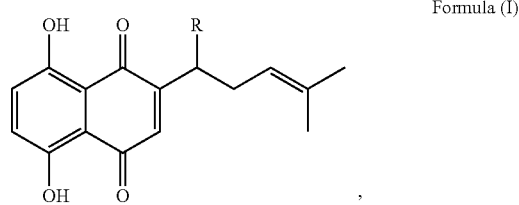

Formula (I)

wherein R is selected from —H, —OH,

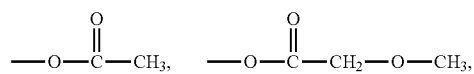

-continued

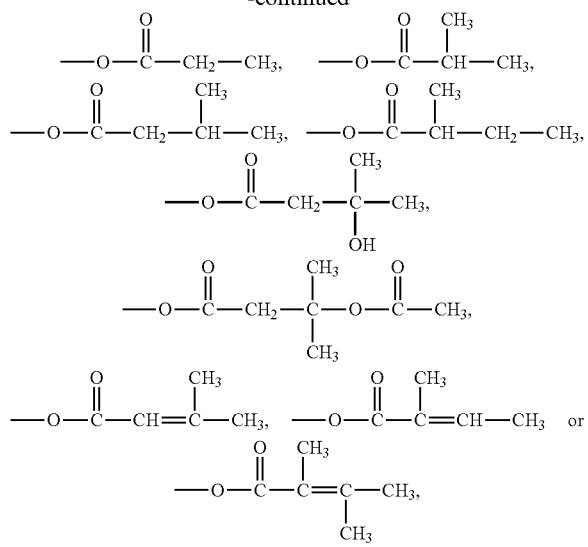

wherein the EGFR-dependent non-small cell lung cancer have an intrinsic or acquired resistance against at least one of gefitinib, erlotinib and/or afatinib.

2. A method of inhibiting EGFR kinase activity in non-small cell lung cancer cells harboring an abnormality in the EGFR gene comprising administering an effective amount of a hydroxynaphthoquinone compound of Formula (I) or a pharmaceutically acceptable salt, solvate or anhydrate thereof:

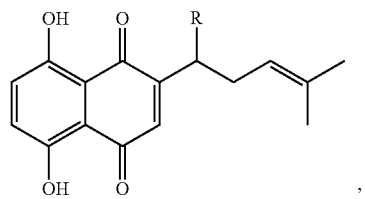

Formula (I)

wherein R is selected from —H, —OH,

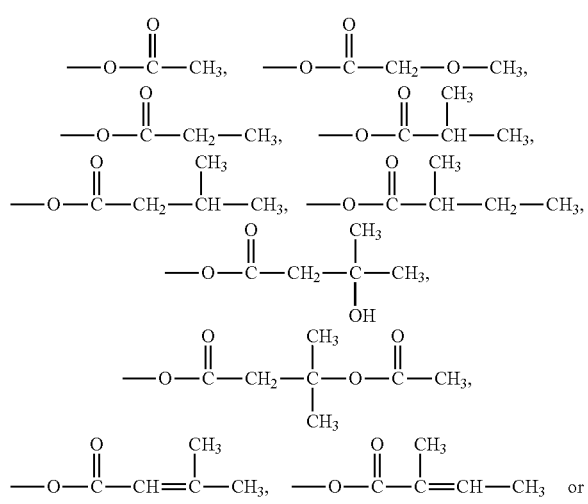

-continued

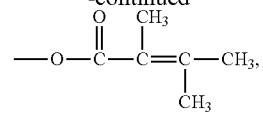

to a subject suffering from EGFR-dependent non-small cell lung cancer,
wherein the non-small cell lung cancer cells have an intrinsic or acquired resistance against at least one of gefitinib, erlotinib and/or afatinib.

3. The method of claim 1 or 2, wherein the compound is a compound of Formula (II):

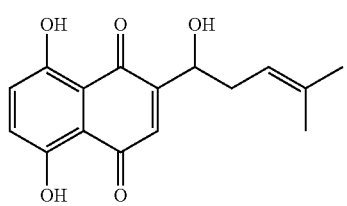

Formula (II)

4. The method of claim 1 or 2, wherein the compound is a compound of Formula (IIa):

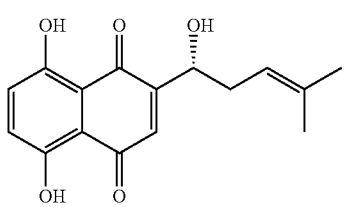

Formula (IIa)

5. The method of claim 1 or 2, wherein the non-small cell lung cancer is an adenocarcinoma.

6. The method of claim 1, wherein the subject is a human and wherein the non-small cell lung cancer comprises cancer cells harboring an abnormality in the EGFR gene resulting from at least one of an exon 19 deletion and/or an exon 21 substitution.

7. The method of claim 6, wherein the subject is a human and wherein the cancer cells harboring an abnormality in the EGFR gene have an intrinsic or acquired resistance at least against gefitinib and/or erlotinib.

8. The method of claim 7, wherein the abnormality in the EGFR gene results from at least one of E746-A750del deletion in exon 19 and/or T790M substitution in exon 20.

9. The method of claim 2, wherein the subject is a human and the EGFR-dependent non-small cell lung cancer cells harbor an abnormality in the EGFR gene resulting from at least one of an exon 19 deletion and/or exon 21 substitution and wherein the EGFR-dependent non-small cell lung cancer cells have an intrinsic or acquired resistance at least against gefitinib and/or erlotinib.

10. The method of claim 9, wherein the abnormality in EGFR gene results from at least one of E746-A750del deletion in exon 19 and/or T790M substitution in exon 20.

11. The method of claim 1 or 2, wherein the compound is administered in form of a pharmaceutical composition comprising the compound and at least one pharmaceutically acceptable excipient selected from at least one of a diluent, a filler, a binder, a disintegrant, a lubricant, a coloring agent, a surfactant or a preservative.

12. A method of targeting non-small cell lung cancer cells harboring an abnormality in the EGFR gene comprising the step of contacting said cells with a hydroxynaphthoquinone compound of Formula (I) or a salt, solvate or anhydrate thereof:

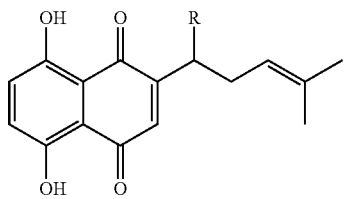

Formula (I)

wherein R is selected from —H, —OH,

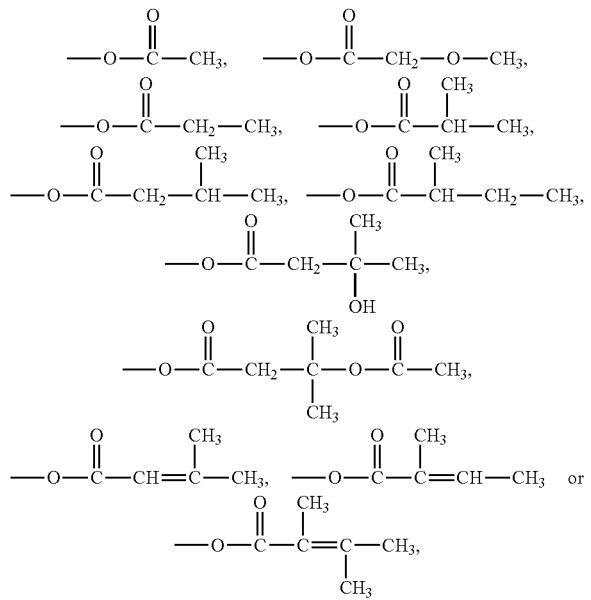

wherein the non-small cell lung cancer cells have an intrinsic or acquired resistance against at least one of gefitinib, erlotinib and/or afatinib.

13. The method of claim 12, wherein apoptosis of the non-small cell lung cancer cells is induced.

14. The method of claim 12, wherein the non-small cell lung cancer cells are from an adenocarcinoma.

15. The method of claim 12, wherein the abnormality in the EGFR gene results from at least one of an exon 19 deletion and/or an exon 21 substitution and wherein the non-small cell lung cancer cells harboring an abnormality in the EGFR gene have an intrinsic or acquired resistance at least against gefitinib and/or erlotinib.

16. The method of claim 15, wherein the compound has an $IC_{50}$ on the non-small cell lung cancer cells harboring an abnormality in the EGFR gene of at most 5 µM and an $IC_{50}$ on non-cancerous lung cells being at least 2 times higher than the $IC_{50}$ on said non-small cell lung cancer cells.

17. The method of claim 12, wherein the compound is used in a concentration of at least 1 µM.

18. The method of claim 12, wherein the compound is a compound having Formula (II):

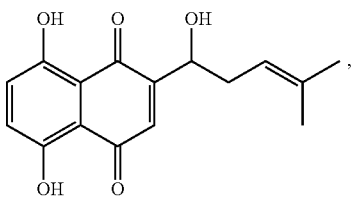

Formula (II)

and wherein the concentration of the compound of Formula (II) is at least 2 µM.

19. The method of claim 12, wherein the compound is a compound having Formula (IIa):

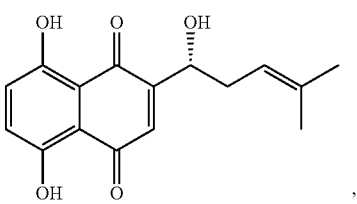

Formula (IIa)

and wherein the concentration of the compound of Formula (IIa) is at least 3 µM.

20. The method of claim 19, wherein the cancer cells are contacted with the compound for at least 12 h.

* * * * *